US007045311B2

(12) United States Patent
Ciambrone et al.

(10) Patent No.: US 7,045,311 B2
(45) Date of Patent: May 16, 2006

(54) WHOLE CELL ASSAY SYSTEMS FOR CELL SURFACE PROTEASES

(75) Inventors: Gary J. Ciambrone, Redwood City, CA (US); Ian Gibbons, Portola Valley, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 477 days.

(21) Appl. No.: 10/281,458

(22) Filed: Oct. 25, 2002

(65) Prior Publication Data

US 2003/0108978 A1    Jun. 12, 2003

Related U.S. Application Data

(60) Provisional application No. 60/337,641, filed on Oct. 25, 2001.

(51) Int. Cl.
*C12Q 1/37*    (2006.01)
*C12Q 1/02*    (2006.01)
*C12Q 1/00*    (2006.01)
*G01N 33/53*    (2006.01)

(52) U.S. Cl. .................... 435/23; 435/24; 435/29; 435/4; 435/968; 435/975

(58) Field of Classification Search ............. 435/23, 435/24, 29, 4, 968, 975
See application file for complete search history.

(56) References Cited

U.S. PATENT DOCUMENTS

| 4,331,590 | A | 5/1982 | Bocuslaski | 260/112 B |
|---|---|---|---|---|
| 4,650,750 | A | 3/1987 | Giese | 435/7 |
| 4,709,016 | A | 11/1987 | Giese | 530/389 |
| 4,780,421 | A | 10/1988 | Kameda | 436/518 |
| 5,057,412 | A | 10/1991 | Rabin | 435/6 |
| 5,340,716 | A | 8/1994 | Ullman | 435/6 |
| 5,360,819 | A | 11/1994 | Giese | 514/538 |
| 5,470,705 | A | 11/1995 | Grossman | 435/6 |
| 5,494,793 | A | 2/1996 | Schindele | 435/6 |
| 5,514,543 | A | 5/1996 | Grossman | 435/6 |
| 5,516,636 | A | 5/1996 | McCapra | 435/6 |
| 5,516,931 | A | 5/1996 | Giese | 560/59 |
| 5,536,834 | A | 7/1996 | Singh | 544/98 |
| 5,565,324 | A | 10/1996 | Still | 435/6 |
| 5,578,498 | A | 11/1996 | Singh | 436/518 |
| 5,580,732 | A | 12/1996 | Grossman | 435/6 |

(Continued)

FOREIGN PATENT DOCUMENTS

WO    WO 93/06121    4/1993

(Continued)

OTHER PUBLICATIONS

Hurtado et al; Neuropharmacology, V. 40(8), pp. 1094-1102, (Jun. 2001).*

(Continued)

*Primary Examiner*—Louise N. Leary
(74) *Attorney, Agent, or Firm*—Stephen C. Macevicz; LeeAnn Gorthey

(57) ABSTRACT

The activity of a cell surface protease, particularly an ADAM, is determined in a rapid and sensitive assay employing a whole cell system. The assays are effective to identify effector molecules that affect the activity of a cell surface protease directly or indirectly, and to screen for therapeutic agents that modulate those effector molecules. The assays can also be used to screen for therapeutic agents that modulate the activity of a cell surface protease associated with a disease or medical condition. Kits comprising at least one component of the present assays are also provided.

47 Claims, 13 Drawing Sheets

U.S. PATENT DOCUMENTS

| | | | | |
|---|---|---|---|---|
| 5,602,273 | A | 2/1997 | Giese | 560/60 |
| 5,604,104 | A | 2/1997 | Giese | 435/7.1 |
| 5,610,020 | A | 3/1997 | Giese | 435/7.1 |
| 5,616,719 | A | 4/1997 | Davalian | 546/334 |
| 5,624,800 | A | 4/1997 | Grossman | 435/6 |
| 5,650,270 | A | 7/1997 | Giese | 435/6 |
| 5,703,222 | A | 12/1997 | Grossman | 536/24.3 |
| 5,705,622 | A | 1/1998 | McCapra | 536/23.1 |
| 5,709,994 | A | 1/1998 | Pease | 435/4 |
| 5,721,099 | A | 2/1998 | Still | 435/6 |
| 5,756,726 | A | 5/1998 | Hemmi | 540/474 |
| 5,766,481 | A | 6/1998 | Zambias | 210/656 |
| 5,777,096 | A | 7/1998 | Grossman | 536/24.3 |
| 5,789,172 | A | 8/1998 | Still | 435/6 |
| 5,807,675 | A | 9/1998 | Davalian | 435/6 |
| 5,807,682 | A | 9/1998 | Grossman | 435/6 |
| 5,843,655 | A | 12/1998 | McGall | 435/6 |
| 5,843,666 | A | 12/1998 | Akhavan-Tafti | 435/6 |
| 5,846,839 | A | 12/1998 | Gallop | 436/518 |
| 5,849,878 | A | 12/1998 | Cantor | 530/391.9 |
| 5,952,654 | A | 9/1999 | Giese | 250/288 |
| 5,958,202 | A | 9/1999 | Regnier | 204/451 |
| 5,986,076 | A | 11/1999 | Rothschild | 536/22.1 |
| 5,989,871 | A | 11/1999 | Grossman | 435/91.1 |
| 6,001,573 | A | 12/1999 | Roelant | 435/6 |
| 6,001,579 | A | 12/1999 | Still | 435/7.1 |
| 6,027,890 | A | 2/2000 | Ness | 435/6 |
| 6,251,581 | B1 | 6/2001 | Ullman | 435/4 |
| 6,255,064 | B1* | 7/2001 | Tindal et al. | 435/23 |
| 6,312,893 | B1 | 11/2001 | Van Ness | 435/6 |
| 6,322,980 | B1 | 11/2001 | Singh | 435/6 |
| 6,331,530 | B1 | 12/2001 | Breslow | 514/58 |
| 6,335,201 | B1 | 1/2002 | Allbritton | 436/63 |
| 6,346,384 | B1 | 2/2002 | Pollner | 435/6 |
| 6,346,529 | B1 | 2/2002 | Floyd | 514/226.2 |
| 6,368,874 | B1 | 4/2002 | Gallop | 436/518 |
| 6,489,116 | B1 | 12/2002 | Wagner | 435/6 |
| 6,627,400 | B1 | 9/2003 | Singh | 435/6 |
| 2002/0037542 | A1 | 3/2002 | Allbritton | 435/7.23 |
| 2003/0108978 | A1* | 6/2003 | Ciambrone et al. | 435/24 |

FOREIGN PATENT DOCUMENTS

| | | |
|---|---|---|
| WO | WO 98/01533 | 1/1998 |
| WO | WO 98/13488 | 4/1998 |
| WO | WO 00/56925 | 9/2000 |
| WO | WO 00/66607 | 11/2000 |
| WO | WO 01/23533 | 4/2001 |
| WO | WO 01/57530 | 8/2001 |

OTHER PUBLICATIONS

Bauvois, "Transmembrane proteases in focus: diversity and redundancy?", J. Leukocyte Biology, 2001; 70:11-17.

Daub et al., "Role of transactivation of the EGF receptor in signaling by G-protein-coupled receptors", Nature, 1996; 397:557-560.

Doedens et al., "Stimulation-induced down-regulation of Tumor Necrosis Factor-alpha converting enzyme", J Biol Chem, 2000; 275:14598-14607.

Hooper et al., "Membrane protein secretases", Biochem J., 1997; 321:265-279.

Howard et al., "Molecular cloning of MADM: a catalytically active mammalian disintegrin-metalloprotease expressed in various cell types", Biochem J., 1996; 317:45-50.

Killar et al., "Adamalysins. A family of metzincins including TNF-alpha converting enzyme (TACE)", Ann NY Acad Sci, 1999; 878:442-452.

Lammich et al., "Constitutive and regulated α-secretase cleavage of Alzheimer's amyloid precursor protein by a disintegrin metalloprotease",.Proc. Natl. Acad. Sci. USA, 1999; 96:3922-3927.

Luttrell et al., "Regulation of tyrosine kinase cascades by G-protein-coupled receptors", Cur Opin Cell Bio, 1999; 11:177-183.

Prenzel, et al., "EGF receptor transactivation by G-protein-coupled receptors requires metalloproteinase cleavage of proHB-EGF", Nature, 1999; 402:884-888.

Primakoff et al., "The ADAM gene family: surface proteins with adhesion and protease activity", Trends Genet., 2000; 16:83-87.

Beaudet, et al., "Homogenous Assays for Single-Nucleotide Polymorphism Typing Using AlphaScreen", Genome Research, 2001, 11:600-608.

Blakely, et al., "Epidermal growth factor receptor dimerization monitored in live cells", Nature Biotechnology, 2000, 18:218-222.

Matko, et al., "Energy Transfer Methods for Detecting for Detecting Molecular Clusters on Cell Surfaces", Methods in Enzymology, 1997, 278:444-462.

Packard BioScience, "Principles of AlphaScreen", Application Note ASC-001, 2001.

Price, et al., "Methods for the Study of Protein-Protein Interactions in Cancer Cell Biology", Methods in Molecular Biology, 2003, 218:255-267.

Sako, et al., "Single-molecule imaging of EGFR signalling on the surface of living cells", Nature Cell Biology, 2000, 2:168-172.

Giese, "Electrophoric Release Tags: Ultrasensitive Molecular Labels Providing Multiplicity", Trends in Analytical Chemistry, vol. 2, No. 7, 1983, pp. 166-168.

Olejnik et al., "Photocleavable Affinity Tags for Isolation and Detection of Biomolecules", Methods in Enzymology, vol. 291, 1998, pp. 135-154.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Joppich-Kuhn et al, "Release Tags: A new class of analytical reagents," Clin. Chem., 28: 1844-1847 (1982).

McVey et al, "Monitoring receptor oligomerization using time-resolved fluorescence resonance energy transfer and bioluminescence resonance energy transfer," J. Biol. Chem., 276: 14092-14099 (2001).

Angers et al, "Detection of $\beta_2$-Adrenergic Receptor Dimerization in Living Cells Using Bioluminescence Resonance Energy Transfer (BRET)", PNAS, Mar. 28, 2000, vol. 97, No. 7, 3684-3689.

Luttrell et al., "Regulation of tyrosine kinase cascades by G-protein-coupled receptors", Our Opin Cell Bio, 1999; 11:177-183.

Prenzel, et al., "EGF receptor transactivation by G-protein-coupled receptors requires metalloproteinase cleavage of proHB-EGF", Nature, 1999; 402:884-888.

Primakoff et al., "The ADAM gene family: surface proteins with adhesion and protease activity", Trends Genet., 2000; 16:83-87.

Beaudet, et al., "Homogenous Assays for Single-Nucleotide Polymorphism Typing Using AlphaScreen", Genome Research, 2001, 11:600-608.

Blakely, et al., "Epidermal growth factor receptor dimerization monitored in live cells", Nature Biotechnology, 2000. 18:218-222.

Matko, et al., "Energy Transfer Methods for Detecting for Detecting Molecular Clusters on Cell Surfaces", Methods in Enzymology, 1997, 278:444-462.

Packard BioScience, "Principles of AlphaScreen", Application Note ASC-001, 2001.

Price, et al., "Methods for the Study of Protein-Protein Interactions in Cancer Cell Biology", Methods in Molecular Biology, 2003, 218-255-267.

Sako, et al., "Single-molecule imaging of EGFR signalling on the surface of living cells", Nature Cell Biology, 2000, 2:168-172.

Giese, "Electrophoric Release Tags: Ultrasensitive Molecular Labels Providing Multiplicity", Trends in Analytical Chemistry, vol. 2, No. 7, 1983, pp. 166-168.

Olejnik et al., "Photocleavable Affinity Tags for Isolation and Detection of Biomolecules", Methods in Enzymology, vol. 291, 1998, pp.135-154.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Joppich-Kuhn et al., "Release Tags: A new class of analytical reagents, " Clin. Chem., 28: 1844-1847 (1982).

McVey et al, "Monitoring receptor oligomerization using time-resolved fluorescence resonance energy transfer and bioluminescence resonance energy transfer, " J. Biol. Chem, 276: 14092-14099 (2001).

Angers et al, "Detection of $\beta_2$ -Adrenergic Receptor Dimerization in Living Cells Using Bioluminescence Resonance Energy Transfer (BRET)", PNAS, Mar. 28, 2000, vol. 97, No. 7, 3684-3689.

\* cited by examiner

SEQUENCE LISTING

```
<160> NUMBER OF SEQ ID NOS: 3

<210> SEQ ID NO 1
<211> LENGTH: 13
<212> TYPE: PRT
<213> ORGANISM: Homo sapiens

<400> SEQUENCE: 1

Glu Val His His Gln Lys Leu Val Phe Phe Ala Glu Asp
 1               5                  10

<210> SEQ ID NO 2
<211> LENGTH: 12
<212> TYPE: PRT
<213> ORGANISM: Homo sapiens

<400> SEQUENCE: 2

Ser Pro Leu Ala Gln Ala Val Arg Ser Ser Ser Arg
 1               5                  10

<210> SEQ ID NO 3
<211> LENGTH: 12
<212> TYPE: PRT
<213> ORGANISM: Homo sapiens

<400> SEQUENCE: 3

Lys Glu Asn Ser Phe Glu Met Gln Lys Gly Asp Gln
 1               5                  10
```

WHOLE CELL ASSAY SYSTEMS FOR CELL SURFACE PROTEASES

This application claims the benefit of U.S. Application Ser. Nos. 60/337,641 filed Oct. 25, 2001 and Ser. No. 09/924,692 filed Aug. 8, 2001, both of which are incorporated herein by reference in their entirety

FIELD OF THE INVENTION

This invention relates to a whole cell assay system for cell surface proteases, such as proteases in the ADAM (a disintegrin and metalloprotease) family.

References

Gurney, M. and Bienkowski, M. J., PCT Pubn. No. WO 01/23533 (April 2001).

Singh, S., PCT Pubn. No. WO 00/66607 (November 2000).

Dyrks, T. et al., PCT Pubn. No. WO 98/13488 (April 1998).

Bauvois, B. Transmembrane proteases in focus: diversity and redundancy? *J Leukocyte Biology* 2001; 70:11–17.

Daub, H., Weiss, F. U., Wallasch, C., and Ullrich, A. Role of transactivation of the EGF receptor in signaling by G-protein-coupled receptors. *Nature* 1996; 379:557–560.

Doedens, J. R., and Black, R. A. Stimulation-induced down-regulation of Tumor Necrosis Factor-alpha converting enzyme. *J Biol Chem* 2000; 275:14598–14607.

Hooper, N. M., Karran, E. H., and Turner, A. J. Membrane protein secretases. *Biochem J* 1997; 321:265–279.

Howard, L., Lu, X., Mitchell, S., Griffiths, S., and Glynn, P. Molecular cloning of MADM: a catalytically active mammalian disintegrin-metalloprotease expressed in various cell types. *Biochem J* 1996; 317:45–50.

Killar, L., White, J., Black, R., and Peschon, J. Adamalysins. A family of metzincins including TNF-alpha converting enzyme (TACE). *Ann NY Acad Sci* 1999; 878:442–452.

Lammich, S., et al. Constitutive and regulated α-secretase cleavage of Alzheimer's amyloid precursor protein by a disintegrin metalloprotease. *Proc. Natl. Acad. Sci. USA* 1999, 96:3922–3927.

Luttrell, L. M., Daaka, Y., and Lefkowitz, R. J. Regulation of tyrosine kinase cascades by G-protein-coupled receptors. *Curr Opin Cell Bio* 1999; 11:177–183.

Prenzel, N., Zwick, E., Daub, H., Leserer, M., Abraham, R., Wallasch, C., and Ullrich, A. EGF receptor transactivation by G-protein-coupled receptors requires metalloproteinase cleavage of proHB-EGF. *Nature* 1999; 402:884–888.

Primakoff, P., and Myles, D. G. The ADAM gene family: surface proteins with adhesion and protease activity. *Trends Genet.* 2000; 16:83–87.

Rosendahl, M. S., Ko, S. C., Long, D. L., Brewer, M. T., Rosenzweig, B., Hedl, E., Anderson, L., Pyle, S. M., Moreland, J., Meyers, M. A., Kohno, T., Lyons, D., and Lichenstein, H. S. Identification and characterization of a pro-Tumor Necrosis Factor-alpha-processing enzyme from the ADAM family of zinc metalloproteases. *J Biol Chem* 1997; 272:24588–24593.

Turner, A. J., and Hooper, N. M. Role for ADAM-family proteinases as membrane protein secretases. *Biochem Soc Trans* 1999; 27:255–259.

Yan, Y., Haynes, S., and Werb, Z. The metalloprotease KUZBANIAN (ADAM-10) mediates the transactivation of EGF receptor by G-protein coupled receptors. *Mol Biol Cell* 2000; 11:S :290a.

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

An ADAM (a disintegrin and metalloprotease) is a transmembrane protein that contains both a disintegrin and a metalloprotease domain (Primakoff et al., 2000). Therefore, ADAMs have both cell adhesion and protease activities. Not surprisingly, a variety of physiological functions have been identified or implicated for ADAMs, including shedding, fertilization, signal transduction and Alzheimer's disease.

For example, ADAMs 17, 10 and 9 have been found to participate in shedding, the release of extracellular domains of membrane-anchored proteins after being cleaved from the remaining part of the proteins by proteases (called sheddases or secretases). One of the best-studied examples of shedding is the release of tumor necrosis factor α (TNF-α), a cytokine involved in the inflammatory response.

TNF-α is synthesized as a 26 kDa membrane-anchored protein, from which a soluble 17 kDa extracellular domain is proteolytically released as active TNF-α. This proteolytic release is catalyzed by TNF-α converting enzyme (TACE or ADAM 17), which also catalyzes the proteolytic cleavage of many other substrates. In fact, cells derived from ADAM 17 knockout mice are also unable to shed the TNF receptor, the adhesion molecule L-selectin, or the Alzheimer's disease amyloid protein, indicating that these proteins are the proteolytic substrates of ADAM 17 as well. The knockout mice themselves would die in utero due to failure to shed embryonic transforming growth factor α.

Similarly, other ADAMs have also been found or predicted to play important roles in normal physiological functions, since the proper proteolytic processing of many cytokines, growth factors, receptors, adhesion molecules and enzymes relies on ADAMs.

Recently, it has also been shown that ADAMs are involved in the signal transduction responses of certain G-protein coupled receptors (GPCRs). As shown in FIG. 1, upon ligand binding to a GPCR, ADAM 10 is activated to cleave the epidermal growth factor (EGF) precursor, PRO-EGF, to mature and active EGF. The resulting EGF, in turn, binds to the EGF receptor and leads to EGF receptor transactivation as well as the subsequent mitogenic signaling response (Daub et al., 1996; Prenzel et al., 1999; Yan et al., 2000). Given the fact that ADAMs participate in many fundamental cellular functions, it is important to be able to determine ADAM activities quickly and efficiently. However, to date, ADAM activities have generally been assayed using traditional biochemical methods, including purification or partially purification of ADAMs from cells, followed by mixing with a substrate and determination of the amount of product produced (see e.g. Rosendahl et al., 1997). These methods are time consuming, require large numbers of cells, and may introduce artifacts during the process of purification. Therefore, an improved method for assaying ADAM activities is desirable.

SUMMARY OF THE INVENTION

The present invention is directed to a rapid and sensitive method of assaying the activity of a cell surface protease, such as an ADAM, using a whole cell system. Thus, whole cells containing an ADAM of interest are combined with a substrate that is cleavable by the ADAM. The amount of cleavage product, which is indicative of the activity of the ADAM, is then determined. Furthermore, as ADAMs mediate the actions of other effector molecules such as GPCRs, this assay can also be used to determine if a candidate effector is capable of modulating the activity of an ADAM. This can be achieved by adding a candidate effector to the basic ADAM assay described above, by transfection, use of particular cell lines defective for a given effector, or other means. A comparison of ADAM activities with and without the candidate effector reveals the impact of the candidate effector on the ADAM. Once an effector is identified, the assay system can be used to further identify agonists and/or antagonists of the effector. For example, if an orphan GPCR is found to up-regulate or down-regulate an ADAM, a battery of candidate ligands can then be added to the assay system comprising the orphan GPCR, the ADAM, and its substrate, to identify the ligand for the orphan GPCR.

The present invention can also be used to determine if a given effector modulates the activity of a designated ADAM. Thus, an effector can be combined with a candidate ADAM and its substrate in a whole cell system, and the amount of cleavage product generated from the substrate is indicative of the effect of the effector on the ADAM being tested. In particular, this method can be used to identify the ADAMs which may be part of the signal transduction pathway of a given GPCR.

In one aspect, the invention provides a method of assaying for the activity of an ADAM (a disintegrin and metalloprotease) in a whole cell system. The method comprises:

(a) selecting a soluble substrate that is specifically cleavable by the ADAM;

(b) combining the soluble substrate with the whole cell system under conditions that allow processing of the substrate to a product by the ADAM; and (c) determining the amount of the product as an indication of the ADAM activity.

Preferably, the substrate contains a detectable label; in one embodiment, the substrate is cleavable by the ADAM to release a product comprising the detectable label. Generally, the substrate and product will be separated prior to, or concurrent with, determining the amount of the product; e.g. by capillary electrophoresis.

A benefit of the assay is that is can be performed on small cell samples. For example, the cell system may comprise fewer than $10^4$, fewer than $10^3$, fewer than 500, or even fewer than 50 cells per assay. In one embodiment, the cells have endogenous levels of the ADAM(s).

The assay can also be carried out in a multiplexed format, for assaying the activities of a plurality of ADAMs. Accordingly, a plurality of such substrates, comprising at least one substrate that is specifically cleavable to a product by each ADAM to be assayed, is combined with the whole cell system, under conditions that allow processing of the substrates to products by the corresponding ADAMs, such that each ADAM produces a different product. The amount of each product is determined, as an indication of the corresponding ADAM activity.

Preferably, each different substrate is labeled with a different detectable label to facilitate quantitation of the respective product. While any detectable labels can be used for this purpose, eTag substrates are particularly suitable for multiplex reactions. Thus, in the multiplex format, each substrate is preferably an electrophoretic probe, comprising an electrophoretic tag, the tag having distinct optical or separation properties with respect to the electrophoretic tag of every other probe used in the assay; and each probe is cleavable by the corresponding ADAM to release the electrophoretic tag. More specifically, each electrophoretic probe is of the form S-L-(D-M), where:

S is a substrate peptide cleavable by the corresponding ADAM;

(D-M) represents an electrophoretic tag, where

D is a detectable group and

M is a mobility modifier effective to impart to the electrophoretic tag a known electrophoretic mobility different from the mobility of the electrophoretic tag of any other probe employed in the assay; and L is a bond or linking group connecting the substrate to the electrophoretic tag.

In another aspect, the invention provides a method for determining the effect of a candidate effector on the activity of an ADAM in a whole cell system. The method comprises:

(a) selecting a soluble substrate that is specifically cleavable by the ADAM;

(b) preparing two mixtures of the whole cell system and the soluble substrate, wherein only one of the mixtures contains the candidate effector;

(c) incubating the mixtures under conditions that allow processing of the substrate to a product by the ADAM, if the ADAM is active;

(d) determining the amount of the product formed in each mixture; and (e) comparing the amount of product formed in the separate mixtures, to determine the effect of the candidate effector on the ADAM activity.

Effectors may include macromolecules, such as proteins, glycoproteins, polysaccharides, glycosaminoglycans, proteoglycans, integrins, enzymes, lectins, selecting, cell-adhesion molecules, toxins, bacterial pili, transport proteins, hormones, antibodies, major histocompatability complexes, immunoglobulin superfamilies, or cadherins. Effectors may also include small molecules, such as putative drugs, monosaccharides, disaccharides, oligosaccharides, amino acids, oligopeptides, nucleosides, nucleotides, oligonucleotides, lipids, retinoids, steroids, or glycopeptides. Preferably, the candidate effector is a receptor, particularly a G-protein coupled receptor (GPCR).

Preferably, the substrate contains a detectable label; in one embodiment, the substrate is cleavable by the ADAM to release a product comprising the detectable label. Generally, the substrate and product will be separated prior to, or concurrent with, determining the amount of the product; e.g. by capillary electrophoresis.

Again, a benefit of the assay is that is can be performed on small cell samples. For example, the cell system may comprise fewer than $10^4$, fewer than $10^3$, fewer than 500, or even fewer than 50 cells per assay. In one embodiment, the cells have endogenous levels of the ADAM(s).

The assay may also be carried out in multiplex format, for determining the effect of a candidate effector on the activity of a plurality of ADAMs from a whole cell system. In this format, a plurality of said soluble substrates, comprising at least one substrate that is specifically cleavable to a product by each ADAM to be assayed, is combined with said whole cell system in two mixtures, where one of the mixtures contains the candidate effector; and the amount of each product formed in the two mixtures is compared, to determine the effect of the candidate effector on the activity of each ADAM. In this format, each substrate is preferably an electrophoretic probe, as described above.

In another aspect, the assays of the invention can be used to determine the effect of a candidate ligand on a receptor in a whole cell system comprising an ADAM, and preferably having endogenous levels of an ADAM, wherein the receptor is known to modulate the activity of said ADAM. The method comprises:

(a) selecting a soluble substrate that is specifically cleavable by the ADAM;

(b) preparing two mixtures of the whole cell system and the soluble substrate, wherein only one of the mixtures contains the candidate ligand;

(c) incubating the mixtures under conditions that allow processing of the substrate to a product by the ADAM, if the ADAM is active;

(d) determining the amount of the product formed in each mixture; and (e) comparing the amount of product formed in the separate mixtures, to determine the effect of the candidate ligand on the receptor.

The receptor may be, for example, a GPCR. Candidate ligands may be selected from putative drugs, oligosaccharides, and oligopeptides.

Again, the substrate preferably contains a detectable label; in one embodiment, the substrate is cleavable by the ADAM to release a product comprising the detectable label. Generally, the substrate and product will be separated prior to, or concurrent with, determining the amount of the product; e.g. by capillary electrophoresis.

Another aspect of the invention is a method of determining the effect of a G-protein coupled receptor (GPCR) on the activity of an ADAM in a whole cell system, including systems having endogenous levels of the ADAM. The method comprises:

(a) selecting a ligand known to modulate activity of the GPCR and a soluble substrate that is specifically cleavable by the ADAM;

(b) preparing two mixtures of the whole cell system and the soluble substrate, wherein only one of the mixtures contains the ligand;

(c) incubating the mixtures under conditions that allow processing of the substrate to a product by the ADAM, if the ADAM is active;

(d) determining the amount of the product formed in each mixture; and (e) comparing the amount of product formed in the separate mixtures, to determine the effect of the GPCR on the ADAM activity.

The GPCR may be, for example, a receptor for endothelin, muscarinic acetylcholine, lysophosphatidic acid, bombesin, vasopressin, bradykinin, glutamate, or thrombin.

The method may be carried out in a multiplex format, to determine the effect of a GPCR on the activity of a plurality of ADAMs in a whole cell system. In this format, a plurality of soluble substrates, comprising at least one substrate that is specifically cleavable by each ADAM to be assayed, is added to said whole cell system in two mixtures, of which only one contains the ligand; and the amount of each product formed in the separate mixtures is compared, to determine the effect of the GPCR on the activity of each ADAM. In this format, each substrate is preferably an electrophoretic probe, as described above.

Based on the diverse functions of ADAMs, the present invention can also be applied for specialized purposes. For example, ADAMs 10 and 17 are among the enzymes which cleave the β-amyloid precursor protein (APP) at the α-secretase site to produce a "good" cleavage product. The production of such "good" product precludes the formation of a "bad" cleavage product of APP, known as the β-amyloid protein, which accumulates in the plaques characteristic of the patients of Alzheimer's disease. Therefore, it is desirable to identify compounds which enhance the formation of such "good" cleavage product. Accordingly, the present invention also provides a method of identifying a compound which enhances cleavage of the β-amyloid precursor protein (APP) at the α-secretase site, comprising:

(a) selecting an enzyme that is capable of cleaving the β-amyloid precursor protein at the α-secretase site in the whole cell system;

(b) selecting a soluble substrate having a cleavable α-secretase site;

(c) preparing two mixtures of the soluble substrate and the whole cell system, wherein only one of the mixtures contains the compound;

(d) incubating the mixtures under conditions that allow cleavage of the substrate at the α-secretase site;

(e) determining the amount of cleavage of the substrate in each mixture; and (f) comparing the amount of cleavage in the separate mixtures, to determine the effect of the compound on cleavage of APP.

The enzyme of step (a) may be, for example, ADAM 17 or ADAM 10. Suitable substrates for step (b) include fragments of human β-amyloid precursor protein containing the cleavage site.

The present invention can also be applied in the diagnosis of diseases or conditions associated with ADAM activities. For example, excessive release of TNF-α is indicative of inflammation, and the release depends on the activity of ADAM 17 (TACE). Thus, a biological sample comprising cells that contain ADAM 17 (particularly cells participating in the inflammation response) can be combined with a soluble substrate bearing the TNF-α cleavage site and the level of cleavage determined. Suitable samples will include, for example, blood and lymphatic fluid.

The assays described herein can be applied to any cell surface protease with a known cleavage substrate. More generally, therefore, the invention provides a multiplexed assay for determining the activity of a plurality of cell surface proteases, in a whole cell system, including systems having endogenous levels of said proteases, the method comprising the steps of:

(a) providing, for each protease being assayed, a soluble substrate specifically cleavable by the protease, (b) combining the substrates with the whole cell system under conditions that allow processing of each substrate to a product by the respective protease; and (c) electrophoretically separating and determining the amount of each product, as an indication of the activity of the corresponding protease;

wherein each substrate is an electrophoretic probe comprising an electrophoretic tag, the tag having distinct optical or separation properties with respect to the electrophoretic tag of every other probe used in the assay; and each probe is cleavable by the corresponding protease to release the electrophoretic tag.

Still another aspect of the present invention provides kits that can be used to determine ADAM activities. For example, a kit comprising a collection of ADAM substrates can be used to identify which ADAM, if any, mediates the function of a GPCR of interest.

The invention also provides kits containing components for use in the above assays. Such a kit contains, for example, a soluble substrate for an ADAM, and a candidate effector for ADAM activity. Preferably, it contains a plurality of soluble substrates, each substrate being specific for a different ADAM, and a plurality of candidate effectors for ADAM activity. A kit comprising the substrate of an ADAM, as well as a plurality of candidate ligands, can be used to identify the agonists and antagonists of an effector which is known to modulate the activity of the particular ADAM. A kit comprising the substrate of an ADAM which is known to cleave the APP at the a-secretase site, as well as a plurality of candidate modulating compounds, can be used to screen drugs for Alzheimer's disease.

In each kit, it is preferable that the ADAM substrate contains a detectable label, particularly an eTag. The substrates may thus be provided as a set of electrophoretic probes; that is, each substrate peptide further comprises an electrophoretic tag, having a detectable group and a mobility modifier effective to impart to the electrophoretic tag a known electrophoretic mobility different from the mobility of the electrophoretic tag of any other substrate employed in the assay.

DETAILED DESCRIPTION OF THE INVENTION

I. Definitions

Figure 1:
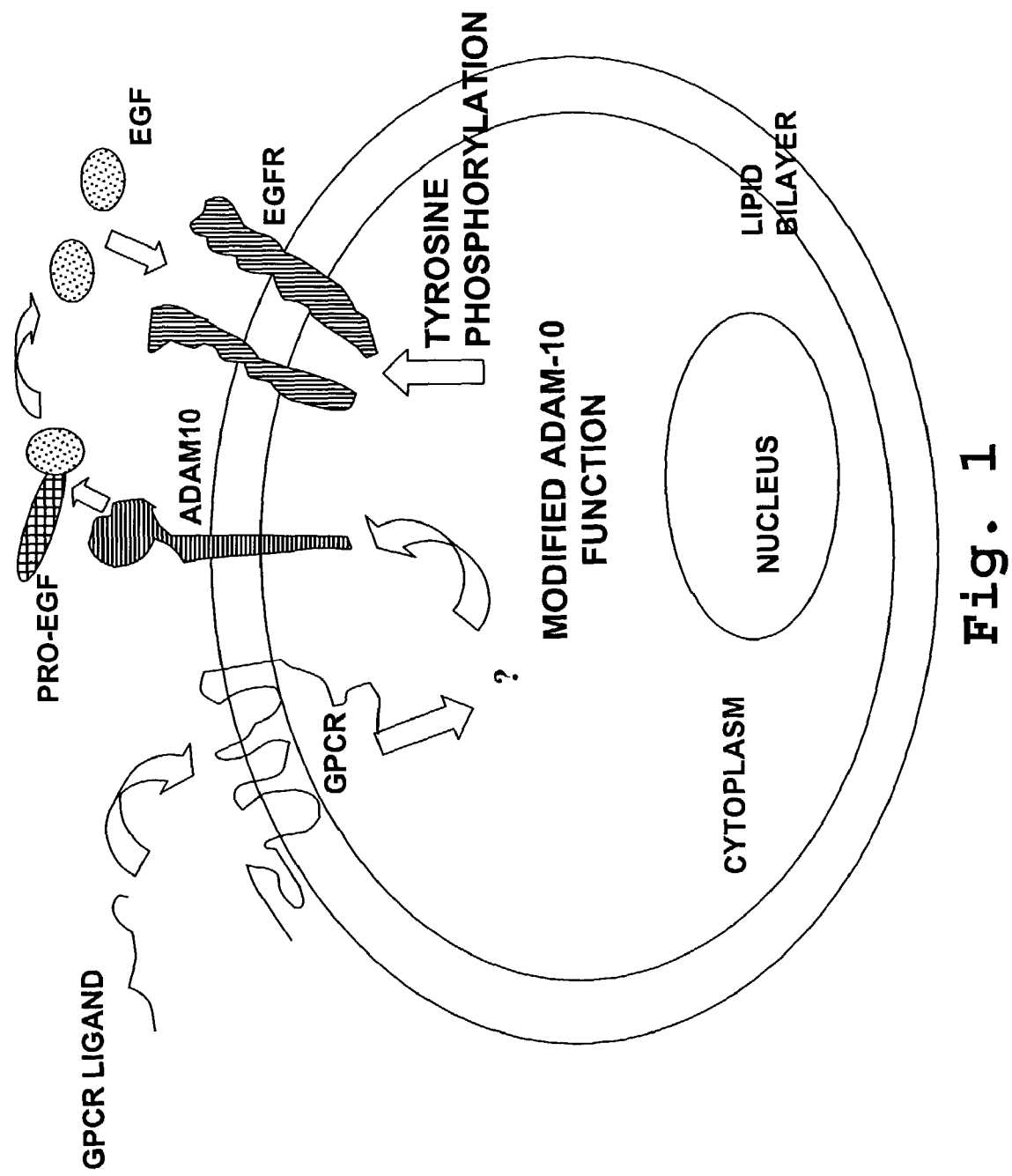
FIG. 1 is a schematic representation of the interaction between a GPCR and ADAM 10. The GPCR, upon binding to its ligand, activates ADAM 10 by an unknown mechanism. The activated ADAM 10 cleaves the EGF precursor, PRO-EGF to the mature EGF. EGF then binds to the EGF receptor (EGFR) and induces tyrosine phosphorylation of the EGFR and other players in the signal transduction pathway to result in proliferation of the cell.

The following terms used in this application are defined as follows unless otherwise indicated.

A "substrate", as used herein, is a substance acted upon by an enzyme in a biochemical reaction. After the biochemical reaction, at least one product is generated due to the action of the enzyme on the substrate. A "soluble substrate" is a substrate which is not membrane bound.

A "whole cell system" is an in vitro assay system comprising whole cells, which is prepared without any effort or reagent to disrupt the cells. For example, cultured cells that have been trypsinized and suspended in solution are a whole cell system, even if a few cells may have been broken during the trypsinization or suspension steps. Preferably, at least about 70% of the cells in a whole cell system are intact. More preferably at least about 80%, and most preferably at least about 90%, of the cells in a whole cell system are intact. The intact cells may be live or dead but are preferably live.

A whole cell system "having endogenous levels" of a protease is one in which the protease level is that occurring naturally in the cell, rather than, for example, obtained via transfection and expression of the protease.

An "ADAM" is a transmembrane protein comprising a disintegrin domain and a metalloprotease domain in the extracellular region of the protein. The disintegrin and protease domains can be identified according to established methods in the art, and in particular by the use of a computer program recognizing the consensus sequences of the disintegrin and protease domains. Dozens of members have been identified in the ADAM family thus far, and the number may increase upon discoveries of new proteins. An ADAM may comprise other sequence motifs in addition to the disintegrin and protease domains, such as additional cell adhesion domains.

As used herein, an ADAM may be an analog of a known ADAM, wherein the analog contains insertional, deletional or substitutional mutations compared to the known ADAM, yet the analog still comprises at least one disintegrin domain and at least one protease domain based on a comparison to the consensus sequence of such domains.

An "effector", as used herein, is a molecule that is capable of modulating the activity of an enzyme, such as an ADAM, directly or indirectly. "Modulating" the activity means increasing or decreasing the activity. A "candidate effector" is a molecule which may act to increase or decrease the activity of an enzyme.

In the context of the present invention, an "electrophoretic probe" refers to a chemical structure containing (1) an electrophoretic "tag" and (2) a substrate for a cell surface protease. Sets of probes, having a known correlation between substrate composition and tag identity, are generally provided for use in the methods described herein. The substrate is a protein or peptide known or believed to be specifically recognized and cleaved by the protease begin assayed. Cleavage of the probe releases the electrophoretic tag (also referred to as an eTag, eTag reporter, or eTag marker), which contains a detectable label and a mobility modifying group. The released eTag may contain a portion of the substrate as well. Electrophoretic tags are described in detail in Section *III.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like. The term "fluorescer" refers to a substance or a portion thereof which is capable of exhibiting fluorescence in the detectable range.

As used herein, the term "spectrally resolvable", in reference to a plurality of fluorescent labels, means that the fluorescent emission bands of the labels are sufficiently distinct, i.e. sufficiently non-overlapping, that electrophoretic tags to which the respective labels are attached can be distinguished on the basis of the fluorescent signal generated by the respective labels using standard photodetection systems, e.g. employing a system of band pass filters and photomultiplier tubes, or the like, as exemplified by the systems described in U.S. Pat. Nos. 4,230,558, 4,811,218, or the like, or in Wheeless et al., in Flow Cytometry: Instrumentation and Data Analysis (Academic Press, NY, 1985), pp. 21–76.

"Capillary electrophoresis" refers to electrophoresis in a capillary tube or in a capillary plate, where the diameter of the separation column or thickness of the separation plate is between about 25–500 microns, allowing efficient heat dissipation throughout the separation medium, with consequently low thermal convection within the medium.

A "sieving matrix" or "sieving medium" refers to an electrophoresis medium that contains crosslinked or non-crosslinked polymers which are effective to retard electrophoretic migration of charged species through the matrix.

"Electrophoretic mobility" refers to the mobility of a charged compound through a defined separation medium, and under defined buffer and electric field conditions. "Different electrophoretic mobilities," as applied to eTags, means that the tags are separable from one another on the basis of different rates of migration in a given electrophoretic medium, e.g., acrylamide gel, and under defined electrophoretic conditions, e.g., standard electrophoretic conditions for separating either positively or negatively charged compounds with different charge/mass ratios.

"Electrophoretic resolution" is a measure of the distinctness, or lack of overlap, of adjacent peaks in an electropherogram. It can be defined, for example, as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of electrophoretic tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like.

A "microfluidic card" is a small microfabricated device in which multiple reactions involving proteins can be carried out and/or the products of the reactions can be separated. A microfluidic card is typically connected with a detection device such that the results of the multiple reactions being separated in parallel can be monitored on-line and recorded.

As used herein, a "solid support" refers to a solid surface such as a magnetic bead, latex bead, microtiter plate well, glass plate, nylon, agarose, acrylamide, and the like.

A "ligand" is a molecule that binds to one or more specific sites of a receptor, thereby changing the activity of the receptor. Representative ligands include, by way of illustration, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, glycopeptides, glycoproteins, glycolipids, proteoglycans and the like, and synthetic analogues or derivatives thereof, including peptidomimetics, natural products or naturally-occurring small molecule organic compounds (i.e., compounds produced by and/or isolated from natural sources, such as soil, water, cells, plants, fungi, animals and the like), synthetic small molecule organic compounds, inorganic ions, organometallic compounds and the like, and mixtures thereof.

The term "natural products" refers to compounds isolated from natural sources, such as cells, plants, fungi, animals and the like. The term "naturally-occurring small molecule organic compounds" refers to natural products that are organic compounds generally having a molecular weight less than about 1000, preferably less than about 500.

A "putative drug" is a compound that may act as an agonist or antagonist of a biological molecule involving in a disease or condition of a mammal. As such, the putative drug may be used to modulate the disease or condition. A putative drug generally has a molecular weight less than about 1000, preferably less than about 500.

A "protein" or a "polypeptide" is used in its broadest sense to refer to a compound of two or more subunit amino acids, amino acid analogs, or other peptidomimetics. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced.

"Specific", in reference to the binding of two molecules or a molecule and a complex of molecules, refers to the specific recognition of one for the other and the formation of a stable complex, as compared to substantially less recognition of other molecules and the lack of formation of stable complexes with such other molecules. Preferably, "specific", in reference to binding, means that to the extent that a molecule forms complexes with other molecules or complexes, it forms at least fifty percent of the complexes with the molecule or complex for which it has specificity. Generally, the molecules or complexes have areas on their surfaces or in cavities giving rise to specific recognition between the two binding moieties. Exemplary of specific binding are antibody-antigen interactions, enzyme-substrate interactions, polynucleotide hybridizations and/or formation of duplexes, cellular receptor-ligand interactions, and so forth.

A "multiplexed assay" refers to an assay in which multiple assay reactions, e.g. simultaneously assays of multiple analytes, are carried out in a single reaction chamber and/or and analyzed in a single separation and detection format.

The term "alkyl" refers to a straight, branched, or cyclic hydrocarbon chain fragment or radical containing between about one and about fifty carbon atoms, more preferably between about one and about twenty carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "lower alkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described are also referred to herein as "alkenes". Similarly, alkyl groups having triple bonds are also referred to herein as "alkynes". However, as used in context with respect to cyclic alkyl groups, the combinations of double and/or triple bonds do not include those bonding arrangements that render the cyclic hydrocarbon chain aromatic.

The term "halo" or "halogen" as used herein refers to the substituents fluoro, bromo, chloro, and iodo.

The term "carbonyl" as used herein refers to the functional group —C(O)—. It will be appreciated that this group can frequently be replaced with well-known carbonyl equivalent groups having similar electronic and/or steric character, such as thiocarbonyl (—C(S)—); sulfinyl (—S(O)—); sulfonyl (—$SO_2$—); phosphonyl (—$PO_2$—), and methine. Other carbonyl equivalents will be familiar to those having skill in organic chemistry.

The term "aryl" as used herein refers to cyclic aromatic hydrocarbon chains having twenty or fewer carbon atoms, e.g., phenyl, naphthyl, phenanthryl, biphenyl and anthryl. One or more carbon atoms of the aryl group may also be substituted with, e.g.: alkyl; aryl; heterocycle; halogen; nitro; cyano; carboxy; hydroxyl, alkoxyl or aryloxyl; thio or mercapto; alkyl- or arylthio; amino; alkylamino; arylamino; dialkyl-, diaryl-, or arylalkylamino; aminocarbonyl; alkylaminocarbonyl; arylaminocarbonyl; dialkylaminocarbonyl; diarylaminocarbonyl or arylalkylaminocarbonyl; carboxyl; alkyl- or aryloxycarbonyl; carboxaldehyde; aryl- or alkylcarbonyl; iminyl; aryl- or alkyliminyl; sulfo; alkyl- or arylsulfonyl; hydroximinyl; aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycloxy, heteroaryloxy, and heteroaralkylthio) are defined by analogy to the above-described terms.

The term "aralkyl" as used herein refers to an aryl group that is joined to a parent structure by an alkyl group as described above, e.g., benzyl, α-methylbenzyl, phenethyl, and the like.

The term "heterocycle" as used herein refers to a cyclic alkyl group or aryl group as defined above in which one or more carbon atoms have been replaced by a non-carbon atom, especially nitrogen, oxygen, or sulfur. Aromatic heterocycles are also referred to herein as "heteroaryl". Example of heterocyclic groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridiniyl, phenazinyl, phenothiazinyl, phenoxazinyl, purinyl, benzimidazolyl, benzthiazolyl, and benzoxazolyl.

II. Assay Methods

A. Assays for Enzymatic Activity

In one aspect, the invention provides a rapid and sensitive method of assaying the activity of a cell surface protease, particularly an ADAM, in a whole cell system. In the assays, whole cells are combined with a soluble substrate that is cleavable by the ADAM of interest, and the amount of the cleavage product, which is indicative of the activity of the ADAM, is determined. No purification of the enzyme is required.

In the present state of the art, ADAMs are generally assayed using partially purified or purified ADAM proteins. The purification process renders such assays time-consuming and error-prone.

The present method also present advantages over the few existing whole cell assays that have been employed in the determination of ADAM activities. These assays involve transfection of a gene coding for the enzyme and/or its substrate, another transmembrane protein, followed by assessment of the amount of the cleavage product in the supernatant. See, for example, Dyrks et al., PCT Pubn. No. WO 98/13488. Clearly, the present method is far more efficient, in that cells having endogenous (i.e. naturally occurring) levels of the cell surfaces proteases are used, and no transfection steps are required.

Figure 2:
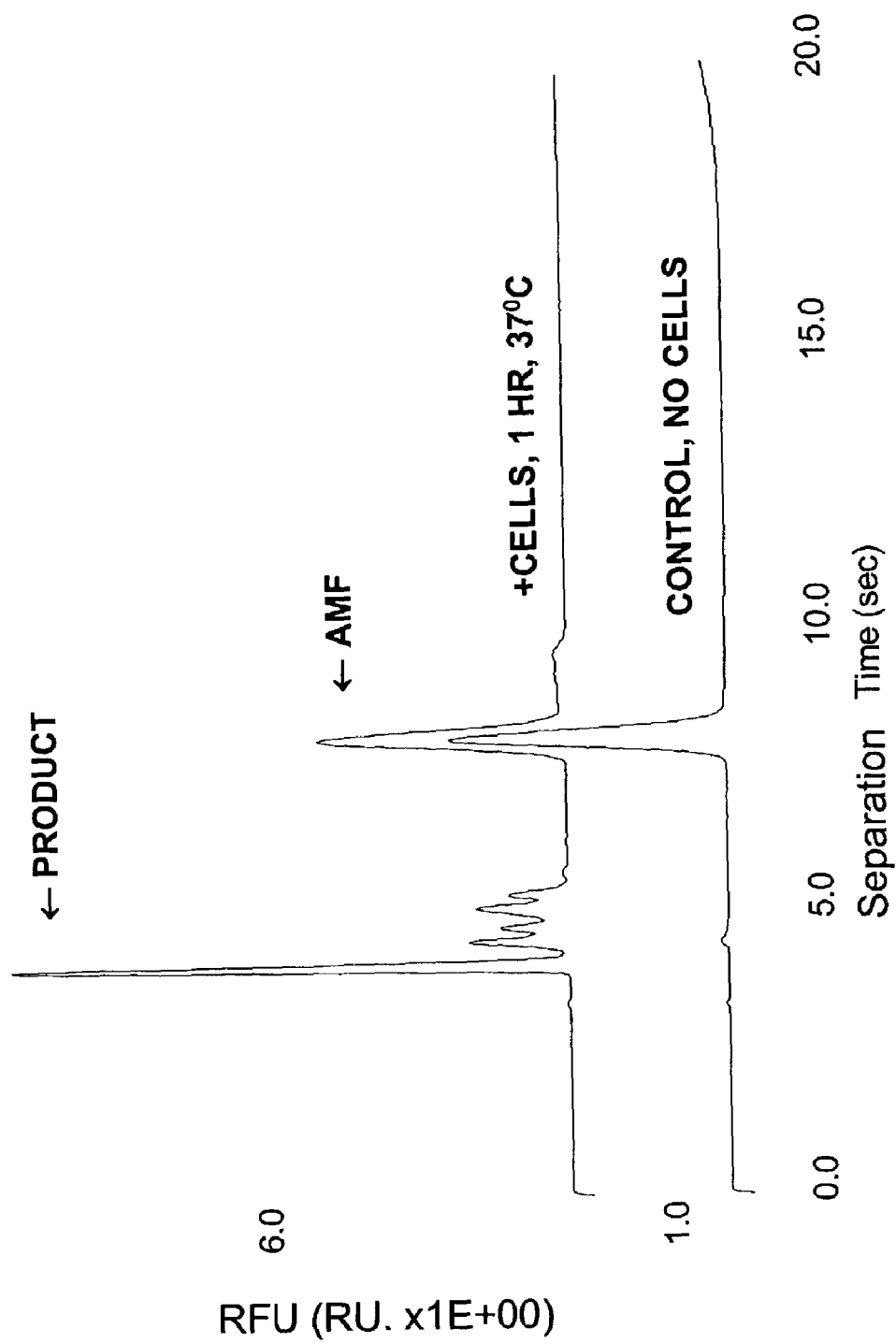
FIG. 2 is an electrophoretic profile of the product and substrate in an ADAM assay carried out in accordance with one embodiment of the invention. In the presence of cells containing ADAM 17, a product migrating at the expected location was formed. RFU stands for relative fluorescence units, an arbitrary scale; AMF is aminomethyl fluorescein, an electrophoretic marker.
Figure 6:
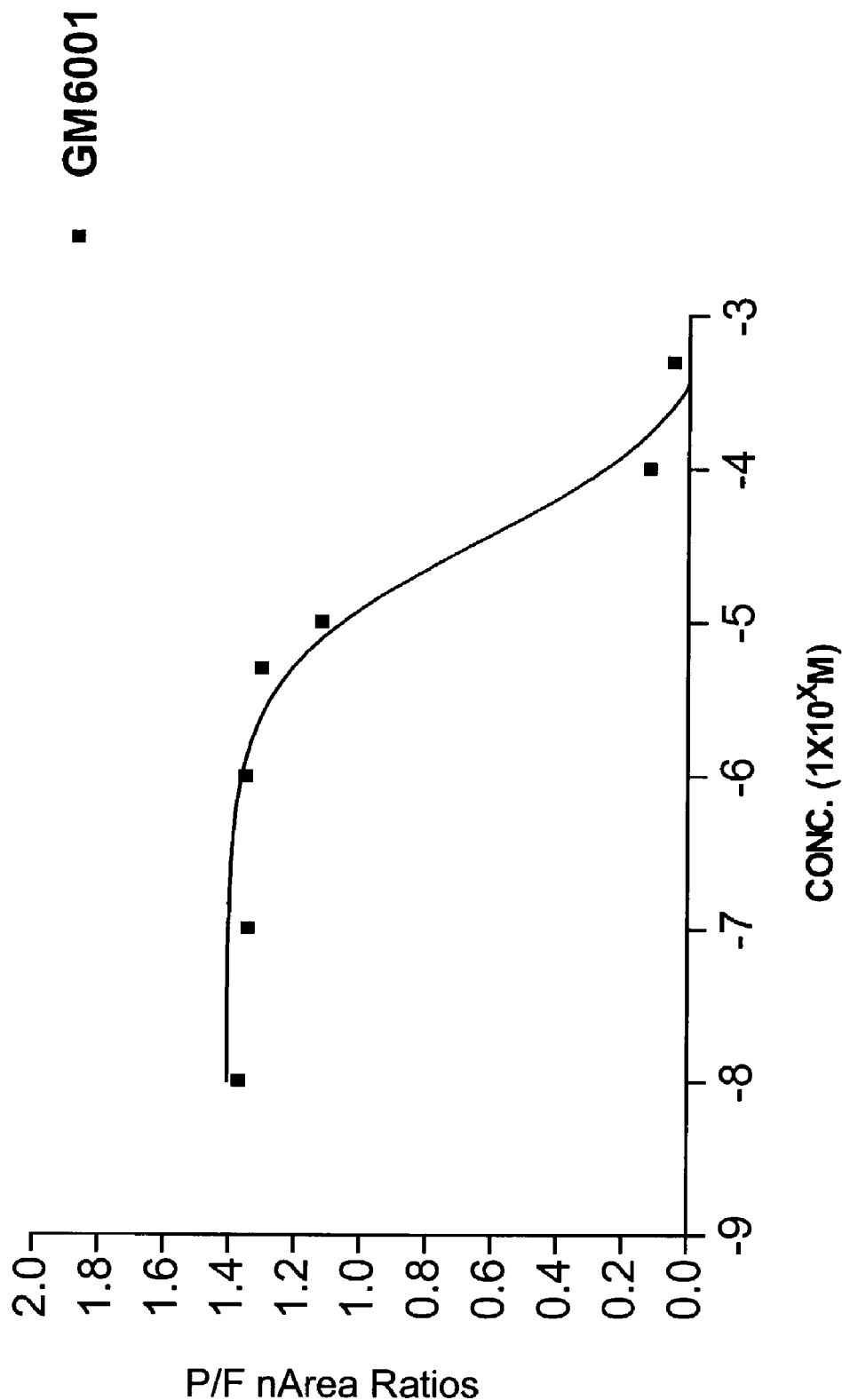
FIG. 6 shows the effect of GM6001, a metalloprotease inhibitor, on the activity of ADAM 17.
Figure 7:
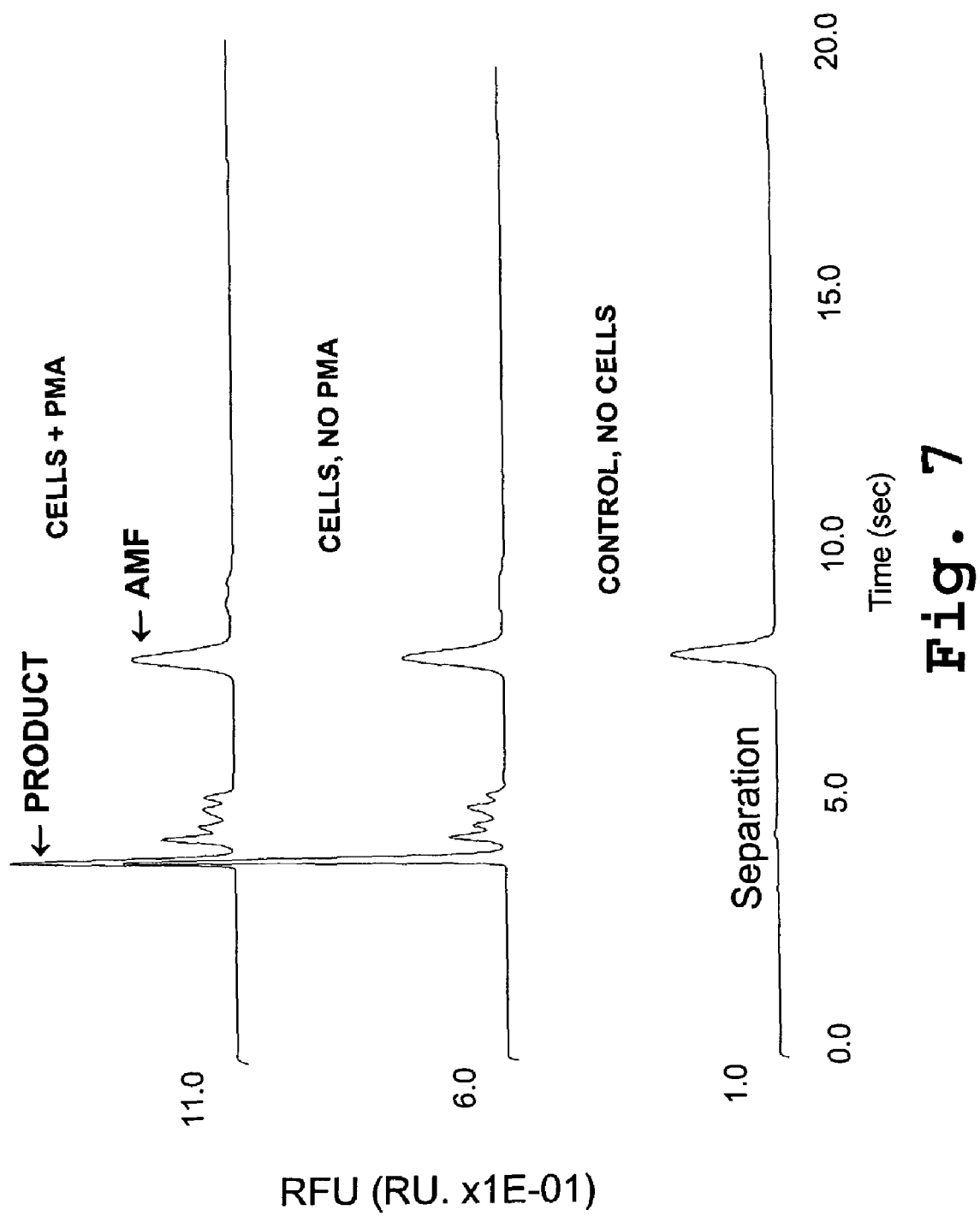
FIG. 7 shows the effect of PMA, which induces internalization of ADAMs, on the activity of ADAM 17.
Figure 8:
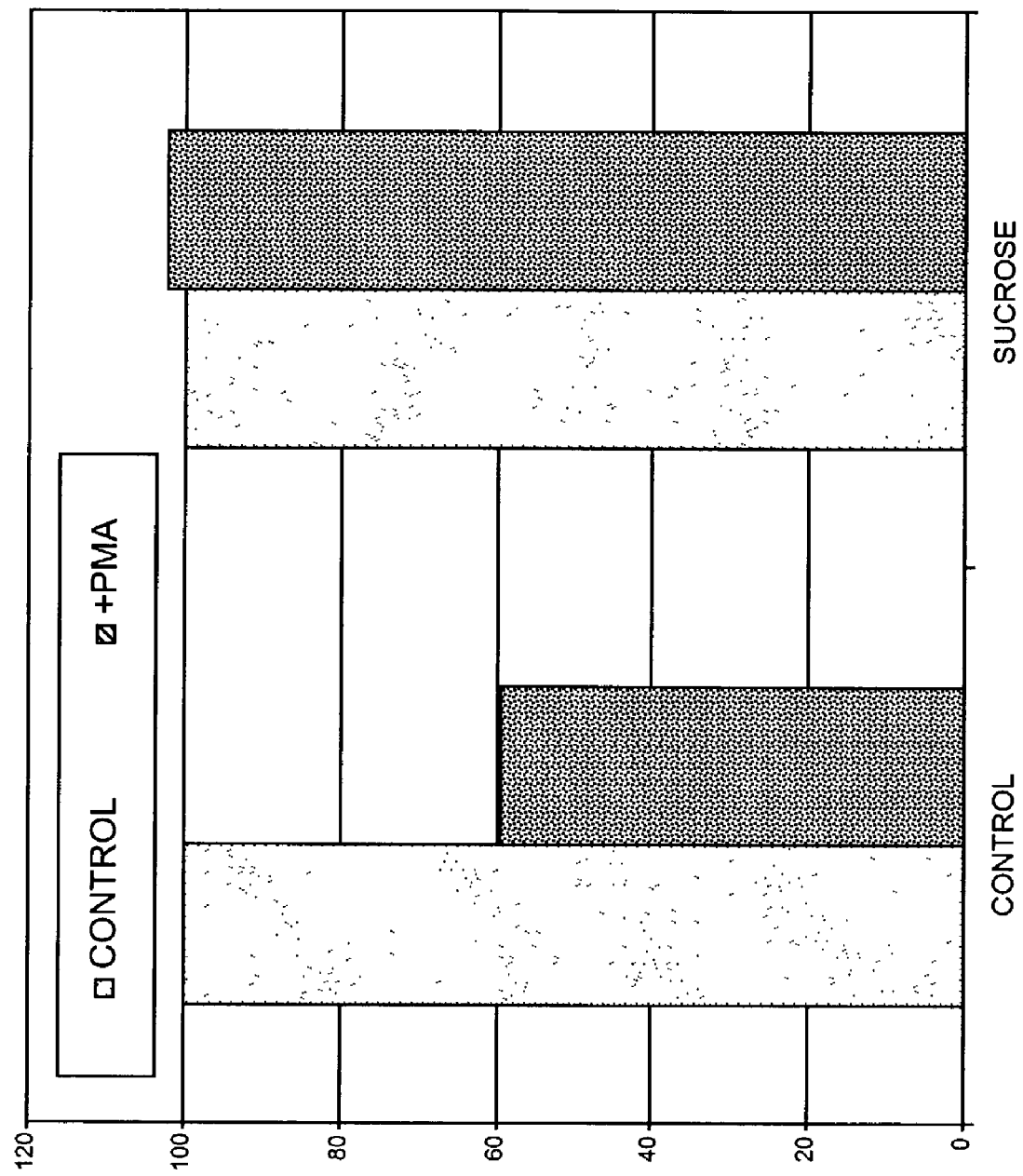
FIG. 8 shows that 450 mM sucrose, which inhibits the effect of PMA on ADAM internalization, restores ADAM 17 activity in the presence of PMA.

Example 1 demonstrates the use of the present method in an assay for ADAM 17 activity. Thus, fluorescein-labeled TNF-α, a substrate specific for ADAM 17, was incubated with whole live THP-1 cells, and the resulting cleavage product was isolated by capillary electrophoresis with on-line fluorescence monitoring. A product of the predicted size and charge was identified, as shown in FIG. 2. Inclusion of a metalloprotease inhibitor (GM6001) in the assay mixture inhibited formation of the cleavage product, as shown in FIG. 6. The level of the product was also reduced when cell surface ADAM 17 molecules were internalized, as induced by addition of PMA; this effect is shown in FIG. 7. The reduction was reversed by adding sucrose, an inhibitor of such internalization, as shown in FIG. 8.

The assay displayed a linear time course from 5 minutes to 3 hours (FIGS. 3–4); therefore, it may be performed in a short time without impairing the accuracy of the assay.

A major advantage provided by the assay is sensitivity. Reliable results were obtained with as few as 40 cells in a 2 μl reaction mixture, which is far less than would be required in a traditional biochemical assay involving lysis of the cells and partial purification of the ADAM. In this regard, it is preferable for the present assay to contain less than about $10^5$ cells per assay, more preferably less than about $10^3$ cells per assay, yet more preferably less than about 500 cells per assay, and most preferably less than about 50 cells per assay.

The amount of the product may be determined using any method established in the art. Preferably, the substrate is labeled with a detectable label and the product determined based on the detectable label. Any detectable label known in the art can be used to label the substrate, including fluorescent, radioactive, enzymatic, and chemiluminescent labels, with fluorescent, enzymatic or chemiluminescent labels being preferred. A particularly suitable detectable label for measuring cleavage activities is a FRET (fluorescence resonance energy transfer) pair, wherein the peptide substrate comprises a fluorescence label at one side and a quencher at the other side of the peptide, and cleavage of the peptide results in increased fluorescence due to separation of the label and the quencher. Accordingly, the substrate and product need not be separated if a FRET pair is used.

Another particularly useful detection system for use in multiplexed applications employs electrophoretic probes and eTags, as described in Section III below. The eTag system employs a plurality of detectable reporter molecules, each of which has a known, predesigned mobility that enables separation of each eTag reporter from all others in a multiplexed assay.

Accordingly, the present invention also encompasses a multiplex assay in which more than one ADAM can be assayed at the same time in a single assay. This can be achieved by providing a group of ADAMs and the cognate substrate for each ADAM, wherein each substrate is labeled with a different label, preferably an eTag. After proper incubation, the cleavage products, preferably different eTag reporters, can be measured in a single procedure, and the activity of each ADAM determined from the level of its cognate cleavage product.

The cleavage product is preferably separated from the substrate prior to determination of the level of the product. Separation can be achieved using chromatographic means, such as size exclusion, affinity, reverse phase chromatography (preferably conducted by HPLC), or any other method established in the art. Preferably, the separation is performed by electrophoresis, most preferably by capillary electrophoresis or on a microfluidic card, which can process many samples in parallel with great speed.

The present invention can be used to identify the substrate for a given cell surface protease. For example, a few known ADAMs are predicted to be. active proteases by their amino acid sequences, yet the substrates for them have not been discovered. Since the present invention allows for rapid and simultaneous screening of numerous compounds, a large collection of peptides can be synthesized and tested with a given ADAM, according to the present invention, to identify which peptide(s) are cleaved by the ADAM. Preferably, a multiplex reaction is performed using multiple candidate peptides, wherein each peptide is cleaved to form a detectable label that can be separated from other cleavage products in the multiplex. Again, the detectable cleavage products preferably comprise electrophoretic tags, as described in Section III below.

B. Assays Identifying Effectors and/or Their Modulators

ADAMs are multi-functional proteins, and their known biological functions continue to increase. For example, it has been reported that ADAM 10 is a component in the signal transduction pathway of G-protein coupled receptors (GPCRs). As shown in FIG. 1, upon ligand binding to a GPCR, ADAM 10 is activated to cleave the epidermal growth factor (EGF) precursor, PRO-EGF, to the mature and active EGF. The resulting EGF, in turn, binds to the EGF receptor and leads to EGF receptor transactivation as well as the subsequent mitogenic signaling response. Therefore, ADAM 10 activity can be used as an indicator of the activity of the GPCR as well as the magnitude of the mitogenic response. The present invention, accordingly, can be used to measure the GPCR activity or the mitogenic signal.

Moreover, the present invention can be used to identify other effectors which modulate the activity of an ADAM to exert a biological action. An effector may be identified whether it increases or decreases the activity of the ADAM, and whether it interacts directly or indirectly with the ADAM. For example, to identify additional effectors for ADAM 10, a battery of candidate effectors can be added to the ADAM 10 assay containing whole cells and an ADAM 10 specific substrate, and the effect of each candidate effector assessed. The ability of a candidate effector to increase or decrease the activity of ADAM 10 would indicate that the candidate is an effector, whether it interacts directly or indirectly with ADAM 10.

It is contemplated that any of these assays may be multiplexed, e.g. to identify the effectors of different ADAMs in a single assay tube or well. Thus, a specific substrate is provided for each ADAM and preferably labeled with a particular detectable label. Preferably, the substrates are in the form of electrophoretic probes, as described in Section III. Whole cells containing all the ADAMs of interest are combined with all these substrates and incubated with candidate effectors. The effect of the candidate effector on each different ADAM can be deduced from the amount of its cognate product.

For example, an effector may increase the activity of ADAM 10, decrease the activities of ADAMs 17 and 9, and have no effect on any other ADAMs. In this case, after cells expressing all the ADAMs of interest are mixed with the respective substrates and the candidate effector, the cleavage product of ADAM 10 would increase, the products of ADAMs 17 and 9 would decrease, and the levels of all other ADAM products would remain the same. Similarly, the effect of another candidate effector on all the ADAMs of interest can be determined in another single assay, and so on. Consequently, a multitude of candidates can be easily screened for their effects on a multitude of ADAMs.

Candidate effectors can be provided by various methods known in the art. For example, a cDNA library can be introduced into the test cell which is known to express the ADAM of interest, and the resulting transformed cells tested for ADAM activity. More specifically, a CDNA library of transmembrane proteins may be assayed for modulation of cell surface ADAM activities. Even more specifically, a collection of cell surface receptors, GPCRs in particular, can be screened to identify effectors of various ADAMs. Soluble factors, which may interact with the extracellular region of an ADAM and thereby modulate the activity of the ADAM, are also good candidate effectors.

Candidate effectors are not limited to cell surface molecules or even large molecules. Small molecules, such as putative drugs, monosaccharides, disaccharides, oligosaccharides, amino acids, oligopeptides, nucleosides, nucleotides, oligonucleotides, lipids, retinoids, steroids, and glycopeptides, may also modulate the activity of an ADAM by interacting directly or indirectly with the ADAM. The present invention provides a method for screening any kind of candidate effector which may modulate the activity of an ADAM.

If an effector is known to modulate the activity of a given ADAM, the present invention can be used to further identify agonists and antagonists of the effector. For example, if a GPCR is known to activate ADAM 10, candidate ligands can be added to an assay system comprising the particular GPCR and ADAM 10, and ADAM 10 activity assessed. This method is particularly useful if an orphan receptor is known to modulate the activity of an ADAM, wherein the method can be used to identify the unknown ligand for the orphan receptor.

The use of the assay to assess the ability of a ligand to activate a GPCR is demonstrated in Example 2. A variety of GPCR ligands, i.e. endothelin-1, LPA and carbachol, were added to different cells known to contain ADAM 10. As expected, each ligand was capable of modulating ADAM 10 activities, presumably through its cognate receptor. The present invention can thus be used to assay for ADAM activities in different cell types, for various receptors, and for ligands. Conversely, the present invention can also be used to identify candidate ADAMs that may be activated or inhibited by a given effector. Thus, a battery of ADAMs and their cognate substrate can be combined with the effector, and the activity of each ADAM compared to that in the absence of the effector. A multiplexing approach is particularly beneficial in this embodiment, since the substrate of each ADAM can be labeled with a different detectable label, preferably by using electrophoretic probes as described in Section III below, and used in the same assay to specifically reveal which ADAM is affected.

Although ADAMs are the preferred protease in the assays described herein, it is contemplated that any cell surface protease may be used in accordance with the present invention. A number of transmembrane proteases have been identified based on their structures and functions, including the ADAMs, ectopeptidases, MT-MMPs, meprins, and secretases (Bauvois, 2001). All of these have a protease domain in the extracellular region, and therefore are suitable subjects in the present assays. Since the functions for many of these proteins are unclear, the present invention can be used to identify their substrates and partners, thereby elucidating the mechanisms by which they may function.

C. Selected Applications

A particular application of the present invention is the identification of a therapeutic agent for Alzheimer's disease. The β-amyloid precursor protein (APP) is an integral membrane protein that can be cleaved by several enzymes to yield different cleavage products (Hooper et al., 1997). One of the cleavage products, βA4 (also known as the β-amyloid protein), accumulates in the brain of Alzheimer's patients and probably plays a key role in the pathogenesis of Alzheimer's disease. The β- and γ-secretases are responsible for the production of βA4, whereas the α-secretase cleaves APP at a different cleavage site, to form another peptide, precluding the formation of βA4. Therefore, a therapeutic agent capable of enhancing the cleavage at the α-secretase site will reduce the formation of βA4 and help to prevent, treat or ameliorate Alzheimer's disease.

The α-secretase has the properties of an integral membrane metalloprotease (Hooper et al., 1997), and both ADAM 10 and ADAM 17 (TACE) have been reported to possess the α-secretase activity (Bauvois, 2001; Lammich et al., 1999). Therefore, the present invention provides a rapid and easily automated method for the screening and identification of therapeutic agents that can enhance the cleavage of APP at the α-secretase site. In this method, a cell containing an α-secretase at the cell surface is combined with a soluble substrate having the α-secretase cleavage site, and various candidate compounds can be added to this whole cell system. A fragment of human APP containing the cleavage site, such as the peptide EVHHQKLVFFAED (SEQ ID NO: 1), can be used as a soluble substrate having the α-secretase cleavage site. A compound that enhances the α-secretase activity can be identified as being capable of increasing the amount of specific cleavage product produced in this system.

Any cell surface protein with the α-secretase activity can be used in this assay to identify drugs for treatment or prevention of Alzheimer's disease. Preferably, the protein is ADAM 10, ADAM 17, or the hu-Asp1 α-secretase (see PCT Pubn. No. WO 01/23533). The assay may be carried out using cells that have endogenous α-secretases, or cells expressing recombinant α-secretases on the cell surface.

The present invention can also be used in the diagnosis of inflammation, since excessive release of TNF-α is indicative of inflammation, and such release depends on the activity of ADAM 17 (TACE). Thus, a biological sample comprising cells that contain ADAM 17 (particularly cells participating in the inflammation response) can be combined with a soluble substrate bearing the TNF-α cleavage site and the level of cleavage determined. Suitable samples will include, for example, blood and lymphatic fluid.

III. Electrophoretic Probes

As discussed above, assays of the invention, particularly multiplexed assays, preferably employ sets of electrophoretic probes which comprise the substrate peptides and cleavage products of the assays. Each electrophoretic probe of a set includes (i) a protease substrate moiety at which a protease in the assay reacts, to release the corresponding eTag product, (ii) a mobility modifier, which imparts to each substrate and its corresponding eTag product, a distinct separation characteristic with respect to other substrates and corresponding eTag products in the set, and (iii) a detectable group, which permits detection of a signal from the substrates and eTag products in the set.

An electrophoretic probe may be represented by the formula:

where

D represents a detectable group;

M is a mobility modifier, the inclusion of which affects the mobility of the eTag probe in a separation method, e.g., electrophoresis;

S is a substrate, which in the present invention is a peptide believed to be capable of specific recognition and cleavage by a cell surface protease; and L is a linking group, which can be a single bond or any chemical structure.

The representation (D, M) indicates that either the detection group or the mobility modifier may be joined to the linking group, i.e., both D-M-L-S and M-D-L-S are contemplated.

The electrophoretic probes are particularly suitable for multiplex reactions, wherein a set of such probes are used, each of which contains a different mobility modifier and/or a different target-binding moiety. The mobility modifier, M, confers upon the molecule containing it a separation characteristic that allows separation of that molecule from all others within a designated set. For example, M may be designed to have a particular charge to mass ratio, and thus a particular electrophoretic mobility in a defined electrophoretic system. In another example, M may be characterized by a unique mass, allowing specific identification in a mass-based separation, e.g., by mass spectrometry. The mobility modifier may be a bond, or it may comprise from 1 to 500 or more atoms. The total number of atoms will depend to a substantial degree on the diversity required to recognize all the targets to be determined. Various substituents may be present on the mobility modifier, including amides, phosphate esters, ethers, esters, thioethers, disulfides, borate esters, sulfate esters, etc. Mobility modifiers are described in more detail in Section A2 below.

A detectable group, D, refers to a chemical group or moiety that is capable of being detected by a suitable detection system. One preferred detection group is a fluorescent moiety or other chromogenic moiety that can be readily detected during or after electrophoretic separation of molecules by illuminating the molecules with a light source in the excitation wavelength and detecting fluorescence emission from the irradiated molecules. Detectable groups are described in more detail in Section A1 below.

The electrophoretic probes employed in the present invention are designed to interact with a cell surface protease, preferably an ADAM. The region of the probe that binds to the ADAM is the substrate S. Upon cleavage of the probe (specifically, the substrate) by a cell surface protease, a structure containing (D,M) is released. The cleavage product may also contain some residue of the substrate and/or linker. The cleavage product, also referred to as an eTag reporter, has, for example, a unique charge-to-mass ratio and thus a unique electrophoretic mobility in a defined electrophoretic system.

A. Electrophoretic Tags (eTags)

The electrophoretic tag, attached to the substrate peptide and cleaved therefrom during the assay, is a water soluble compound that is stable with respect to the conditions employed for cleavage and release and that includes a detection or reporter group. Otherwise, the tag may vary widely in size and structure. Preferably, the tag carries a charge at neutral pH and has a molecular weight in the range of from about 150 to about 10,000 daltons, more preferably, from about '150 to about 5000 daltons, and most preferably, from about 150 to 2500 daltons. Preferred structures are described more fully below. Preferably, the detection group generates an electrochemical, fluorescent, or chromogenic signal. Most preferably, the detection group generates a fluorescent signal.

A description of eTags is also provided in co-owned U.S. application Ser. No. 09/824,851, published on Dec. 13, 2001 as US Application No. 20010051340, which is hereby incorporated by reference in its entirety. The descriptions therein are primarily directed to phosphoramidate-based eTags, but can be adapted to other structures.

Each of the plurality of electrophoretic tags employed in a single multiplexed assay has a distinct charge-to-mass ratio and/or a unique optical property with respect to the other members of the plurality. Preferably, the optical property is a fluorescence property, such as emission spectrum, fluorescence lifetime, or the like. More preferably, the fluorescence property is an emission spectrum. For example, each electrophoretic tag of a plurality of tags may have the same fluorescent emission properties, but will differ from the others by virtue of unique charge-to-mass ratios. On the other hand, two or more of the electrophoretic tags of a plurality of tags may have identical charge-to-mass ratios, but they will have unique fluorescent properties, e.g. spectrally resolvable emission spectra, so that all the members of the plurality are distinguishable by the combination of electrophoretic separation and fluorescence measurement.

A preferred structure of an electrophoretic tag can be represented by (M,D), where M is a mobility-modifying moiety and D is a detection moiety. The notation "(M,D)" is used to indicate that the ordering of the M and D moieties may be such that either moiety can be adjacent to the point of linkage to the probe.

A1. Detection Moiety D

Detection moiety D is any moiety that allows the product and substrate to be detected, preferably quantitatively, following separation in the separation medium. For spectrophotometric detection, fluorophores or dyes may be used. Radiolabeled reporters are another class of suitable reporters. Alternatively, the reporter may be a catalytic moiety that is effective to catalyze a detectable reaction in the presence of suitable reaction components, such as described in co-owned U.S. patent application Serial No. 60/293,821, filed May 26, 2001. [PCT Appn. No. WO 2002US16726, filed May 24, 2002]

Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, 8th ed., (Molecular Probes, Eugene, 2002); Lee et al., U.S. Pat. No. 6,191,278; Lee et al., U.S. Pat. No. 6,372,907; Menchen et al., U.S. Pat. No. 6,096,723; Lee et al., U.S. Pat. No. 5,945,526; Lee et al., Nucleic Acids Research, 25: 2816–2822 (1997); Hobb, Jr., U.S. Pat. No. 4,997,928; Khanna et al., U.S. Pat. No. 4,318,846; Reynolds, U.S. Pat. No. 3,932,415; Eckert et al., U.S. Pat. No. 2,153,059; Eckert et al., U.S. Pat. No. 2,242,572; Taing et al., PCT Pubn. No. WO 02/30944; Stryer, Science 162, 526 (1968) and Brand et al, Ann. Rev. Biochem. 41, 843 (1972). Further specific exemplary fluorescent dyes include 5- and 6-carboxyrhodamine 6G; 5- and 6-carboxy-X-rhodamine, 5- and 6-carboxytetramethylrhodamine, 5- and 6 -carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7', 8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein. Most preferably, D is a fluorescein or a fluorescein derivative. Many of these compounds are commercially available with substituents on the phenyl group which can be used as the site for bonding or as the bonding functionality. For example, amino and isothiocyanate substituted fluorescein compounds are available.

Other fluorescers include nitrogen-containing macrocycles, e.g. derivatives of porphyrins, azaporphyrins, corrins, sapphyrins and porphycenes and other like macrocycles, which contain electrons that are extensively delocalized. The azaporphyrin derivatives include phthalocyanine, benzotriazaporphyrin and naphthalocyanine and their derivatives.

In some instances, fluorescent fusion proteins may be employed, using green fluorescent protein or other fluorescent protein fused to a polypeptide substrate.

The detection moiety of (M,D) may generate a fluorescent signal by an energy transfer mechanism. Preferably, in this aspect, D has the form "$D_1$-g-$D_2$" where $D_1$ and $D_2$ are acceptor-donor pairs of molecules, e.g. Wu et al., Anal. Biochem. 218:1–13 (1994), and g is a rigid linker that maintains $D_1$ and $D_2$ at a substantially constant distance. Guidance in selecting the rigid linker may be found in Wu et al. (cited above) and in U.S. Pat. Nos. 5,863,727; 5,800, 996; 5,945,526; and 6,008,379. Either $D_1$ or $D_2$ may be the acceptor and the other the donor molecule in the pair. Exemplary energy transfer detection moieties for use with the invention are disclosed in Lee et al., U.S. Pat. No. 5,945,526; Lee et al., Nucleic Acids Res. 25:2816–2822 (1997); Taing et al., PCT Publication WO 02/30944; and like references. Preferably, rigid linker, g, is selected so that the distance between $D_1$ and $D_2$ is maintained at a substantially constant distance within the range of from 10–100 Angstroms. A wide variety of linking groups may be employed with the proviso that the linkage is stable to the presence of singlet oxygen. Preferably, $D_1$ and $D_2$ are selected from the set of fluorescein, rhodamine, rhodamine 6G, rhodamine 110, rhodamine X, tetramethylrhodamine, and halogenated derivatives thereof. More preferably, $D_1$ and $D_2$ are both fluorescein dyes.

In one aspect, g may be selected from any of $R_1$–$R_2$–$R_1$ and $R_1$–$R_2$—C(=O)—$X_1$–$R_3$, the latter being present in either orientation with respect to $D_1$ and $D_2$; where $X_1$ is O, S, or NH; $R_1$ is ($C_1$–$C_5$ alkyldiyl, $X_1$, C(=O)) such that the moieties in parentheses are arranged in any linear order; $R_2$ is a 5 to 6 membered ring selected from the group consisting of cyclopentene, cyclohexene, cyclopentadiene, cyclohexadiene, furan, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene; and $R_3$ is $C_1$–$C_5$ alkyldiyl.

An eTag may also contain, instead of a detectable group D, a functionality allowing it to bind to a detectable group D after reaction with a sample is complete. In one embodiment, a plurality of different functionalities are used for different binding members, for reaction with a label, and the different labels have corresponding functionalities that react with one of the first functionalities. For example, where the first functionalities include thiols, carboxyl groups, aldehydes and olefins, the labels could include activated olefins, alcohols, amines and thiol groups, respectively. By employing removable protective groups for one or more of the functionalities, the protective groups may be removed stepwise and the labels added stepwise, to avoid cross-reactivity.

A2. Mobility Modifier M

The mobility modifiers is selected to impart to the substrate and corresponding eTag a unique separation characteristic with respect to each other and all other substrates and corresponding eTags in the set. Where the separation characteristic is electrophoretic mobility, the mobility modifier will preferably be selected to impart a unique charge/mass ratio and/or shape to each substrate and product. Where the separation characteristic is chromatographic separation, the different mobility modifiers will have different hydrophobicities, charge, molecular weight, and/or size. For mass spectrometric analysis, the different mobility modifiers will have different masses.

Modifiers suitable for imparting different electrophoretic separation characteristics have been detailed in co-owned PCT patent application WO 00/66607, published Nov. 9, 2000, and incorporated herein by reference. Such modifiers typical have repeating subunit groups that impart unique charge/mass ratios to each different modifier.

In general, M is a chemical group or moiety having a particular charge-to-mass ratio and thus a particular electrophoretic mobility in a defined electrophoretic system. In a set of n electrophoretic probes, each unique mobility modifier may be designated $M_j$, where j=1 to n, and n has a value as described above. That is, n is generally from 5 to 200, and more preferably, from 5 to 100, or 5 to 75, or from 5 to 50, or from 10 to 30.

The mobility-modifying moiety may be considered to include a mass-modifying region and/or a charge-modifying region, or a single region that acts as both a mass- and charge-modifying region. The mobility-modifying moiety may have one or more of the following characteristics: (i) a unique charge-to-mass ratio due to variations in mass, but not charge; (ii) a unique charge-to-mass ratio due to changes in both mass and charge; and (iii) a unique charge-to-mass ratio of between about –0.0001 and about 0.5, usually, about –0.001 and about 0.1. As noted above, D is typically the same among a set or plurality of different electrophoretic probes, but it may also differ among probe sets, contributing to the unique electrophoretic mobilities of the released electrophoretic tag.

The size and composition of mobility-modifying moiety, M, can vary from a bond to about 100 atoms in a chain, usually not more than about 60 atoms, and more usually not more than about 30 atoms, where the atoms are preferably selected from carbon, oxygen, nitrogen, phosphorous, boron and sulfur. Generally, when other than a bond, the mobility-modifying moiety has from about 0 to about 40, more usually from about 0 to about 30, heteroatoms, which in addition to the heteroatoms indicated above may include halogen or another heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (including ammonium), phosphonium, sulfonium, oxonium, etc., where substituents are generally aliphatic of from about 1–6 carbon atoms, the total number of carbon atoms per heteroatom usually being less than about 12, preferably less than about 9. Other substituents may include hydroxyl groups, including phenolic groups, carboxyl groups, esters, amides, phosphates, and heterocycles. The charged mobility-modifying moieties generally have only negative or only positive charges, although one may have a combination of charges, particularly where a region to which the mobility-modifying moiety is attached is charged and the mobility-modifying moiety has the opposite charge.

In various embodiments, M may be an oligomer, having monomers of the same or different chemical characteristics, e.g., nucleotides and amino acids. The mobility-modifying moieties may comprise a single type of monomer that provides the different functionalities for oligomerization and that carries a charge. Alternatively, two or more different monomers may be employed. Substituted diols may be used, where the substituents are charged and dibasic acids. Illustrative of such oligomers is the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acids, which dibasic acids include the inorganic dibasic acids indicated above, as well as organic dibasic acids, such as oxalic acid, malonic acid, succinic acid, maleic acid, fumaric acid, carbonic acid, etc. Instead of using esters, amides may be used, and amino acids or diamines and diacids may be employed. Alternatively, the hydroxyls or amines may be linked with alkylene or arylene groups.

Pluralities of electrophoretic tags may include oligopeptides for providing the charge, particularly oligopeptides of from 2–6, usually 2–4 monomers, either positive charges, resulting from lysine, arginine and histidine, or negative charges, resulting from aspartic and glutamic acid. Unnatural or synthetic amino acids, such as such as taurine, phosphate substituted serine or threonine, S-α-succinylcysteine, can also be used, as well as co-oligomers of diamines and amino acids, etc. The charge-imparting moiety may also include thioacids and other carboxylic acids having from one to five carbon atoms. The charge imparting moiety may have from 1 to about 30, preferably 1 to about 20, more preferably, 1 to about 10 amino acids per moiety and may also comprise 1 to about 3 thioacids or other carboxylic acids. However, when used with an uncharged sub-region, the charged sub-region will generally have from 1 to about 4, frequently 1 to about 3 amino acids.

By using monomers having multiple charges, a lower number of monomers can be employed to provide for mobility variation with changes in molecular weight. Of particular interest are polyolpolycarboxylic acids having from about two to four of each functionality, such as tartaric acid, 2,3-dihydroxyterephthalic acid, 3,4-dihydroxyphthalic acid, $D^5$-tetrahydro-3,4-dihydroxyphthalic acid, etc. To provide for an additional negative charge, these monomers may be oligomerized with a dibasic acid, such as a phosphoric acid derivative to form the phosphate diester. Alternatively, the carboxylic acids can be used with a diamine to form a polyamide, while the hydroxyl groups can be used to form esters, such as phosphate esters, or ethers such as the ether of glycolic acid, etc.

To vary mobility, various aliphatic groups of differing molecular weight may be employed, such as polymethylenes, polyoxyalkylenes, polyhaloaliphatic or aromatic groups, polyols, e.g., sugars, where the mobility will differ by at least about 0.01, more usually at least about 0.02 and more usually at least about 0.5. Methods of forming selected-length polyethylene oxide-containing chains are well known, see, e.g. Grossman et al., U.S. Pat. No. 5,777,096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. Additionally, polypeptides of selected lengths and amino acid composition (i.e., containing naturally occurring or man-made amino acid residues), as homopolymers or mixed polymers may be used. Various oligomers may be synthesized on a support or produced by cloning or expression in an appropriate host. Conveniently, polypeptides can be produced having only one cysteine (for a thiol functionality), serine/threonine/tyrosine (hydroxyl), aspartic/glutamic acid (carboxyl), or lysine/arginine/histidine (amino), other than an end group, providing a unique functionality which may be differentially functionalized. By using protective groups, a side-chain functionality can be distinguished from a terminal amino acid functionality. Also, by appropriate design, one may provide for preferential reaction between the same functionalities present at different sites on the mobility-modifying moiety. Whether one uses synthesis or cloning for preparation of oligopeptides, is to a substantial degree dependent on the length of the mobility-modifying moiety.

(M, D) moieties can be conveniently constructed from one or more of the same or different common or commercially available linking, cross-linking, and labeling reagents that permit facile assembly, especially using a commercial DNA or peptide synthesizer for all or part of the synthesis. In this aspect, (M, D) moieties are made up of subunits usually connected by phosphodiester and amide bonds. Exemplary precursors that form amide bonds include Fmoc- or Boc-protected amino acid precursors, and derivatives thereof, e.g. as commercially available from AnaSpec, Inc. (San Jose, Calif.). Exemplary precursors that form phosphodiester bonds include various commercially available substituted and protected phosphoramidites, e.g. 6-(4-monomethoxytritylamino)hexyl-(2-cyanoethyl)-(N,N-diisopropyl)-phosphoramidite, (S-trityl-6-mercaptohexyl)-(2-cyanoethyl)-(N,N-diisopropyl)-phosphoramidite, 5'-fluorescein phosphoramidite, 1,3-bis-[5-(4,4'-dimethoxytrityloxy) pentylamido]propyl-2-[(2-cyanoethyl)-(N,N-diisopropyl)]-phosphoramidite, etc.

Mobility modifiers may also be constructed from such commercially available reagents as succinimidyl trans-4-(maleimidylmethyl) cyclohexane-1-carboxylate (SMCC), succinimidyl 3-(2-pyridyldithio)propionate (SPDP), succinimidyl acetylthioacetate, Texas Red-X-succinimidyl ester, 5- and 6-carboxy tetramethylrhodamine succinimidyl ester, bis-(4-carboxypiperidinyl) sulfonerhodamine di(succinimidyl ester), 5- and 6-((N-(5-aminopentyl)aminocarbonyl) tetramethylrhodamine, succinimidyl 4-(p-maleimidophenyl) butyrate (SMPB); N-γ-maleimidobutyryl-oxysuccinimide ester (GMBS); p-nitrophenyl iodoacetate (NPIA); 4-(4-N-maleimidophenyl)butyric acid hydrazide (MPBH); and like reagents. The above reagents are available from Glen Research (Sterling, Va.), Molecular Probes (Eugene, Oreg.), Pierce Chemical, and like reagent providers. Use of the above reagents in conventional synthetic schemes is well known in the art, e.g. Hermanson, Bioconjugate Techniques (Academic Press, New York, 1996).

In another aspect, (M,D) moieties are constructed from chemical scaffolds used in the generation of combinatorial libraries. For example, the following references describe scaffold compounds useful in generating diverse mobility modifying moieties: peptoids (PCT Publication WO 91/19735, Dec. 26, 1991), encoded peptides (PCT Publication WO 93/20242, Oct. 14 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., *Proc. Nat. Acad. Sci. U.S.A.* 90: 6909–6913 (1993)), vinylogous polypeptides (Hagihara et al., *J Am. Chem. Soc.* 114: 6568 (1992)), nonpeptidal peptidomimetics with a β-D-glucose scaffolding (Hirschmann, R. et al., *J. Am. Chem. Soc.* 114: 9217–9218 (1992)), analogous organic syntheses of small compound libraries (Chen, C. et al., *J Am. Chem. Soc.* 116:2661(1994)), oligocarbamates (Cho, C. Y. et al., *Science* 261: 1303(1993)), peptidyl phosphonates (Campbell, D. A. et al., J. Org. Chem. 59:658(1994)); Cheng et al., U.S. Pat. No. 6,245,937; Heizmann et al., "Xanthines as a scaffold for molecular diversity," *Mol. Divers.* 2:171–174 (1997); Pavia et al., *Bioorg. Med. Chem.* 4:659–666 (1996); Ostresh et al., U.S. Pat. No. 5,856,107; Gordon, E. M. et al., *J. Med. Chem.* 37:1385 (1994); and the like. Preferably, in this aspect, D is a substituent on a scaffold and M is the rest of the scaffold.

The mobility modifier may also comprise an alkylene or aralkylene group, the latter comprising a divalent aliphatic group having about 1 to about 2 aliphatic regions and about 1 to about 2 aromatic regions, generally benzene, where the groups may be substituted or unsubstituted, usually unsubstituted, comprising from 2 to about 16, more usually 2 to about 12, carbon atoms. Such mobility modifiers may be used to link one or more fluorescers to a monomeric unit, e.g., an amino acid. The mobility-modifying moiety may terminate in a carboxy, hydroxy or amino group, forming an ester or amide upon conjugation. By varying the substituents on the fluorescer(s), one can vary the mass in units of at least about 5 or more, usually at least about 9. To add hydrophilicity, alkyleneoxy groups may be used in place of aralkylene groups.

In some embodiments, the electrophoretic moieties need not be charged, but merely differ in mass. Thus, the same or similar monomers can be used, where the functionalities are neutral or converted to neutral moieties, such as esters and amides of carboxylic acids. Also, the electrophoretic moieties may be varied by isotopic substitution, such as $^2$H, $^{18}$O, $^{14}$C, etc.

Diversity in sets of probes or eTags can also be achieved via the chemical and optical characteristics of the label, the use of energy transfer complexes, and variations in the chemical nature of the mobility-modifying moiety which affect mobility, e.g. via folding, interaction with the solvent and ions in the solvent, and the like.

Where the substrate moiety is a biopolymer, such as an oligopeptide, this moiety itself may be varied to provide differences in separation characteristics, that is, to function as the mobility modifier. For example, amino acids in an oligopeptide that are not related to substrate interaction with the enzyme may be substituted to increase or reduce total molecular weight or size or vary the charge of the oligopeptide. In constructing substrates of this type, one first identifies the amino acids necessary for enzyme specificity, then makes amino acid substitutions, deletions, or additions designed to alter electrophoretic mobility. After constructing a new substrate, it must be tested to confirm that substrate kinetics are unchanged, or if changed, the kinetics must be standardized to a known substrate. A combination of substrate modification and separate mobility modifier may also be employed.

A3. Multiple Electrophoretic Tags

It may be advantageous to effect the release of multiple electrophoretic tag reporters for a binding event involving an individual target molecule. In a sense, this results in an amplification of signal. Where the substrate has a plurality of sites for attachment, a plurality of electrophoretic tags can be attached, to provide probes that can release from 2–1000, preferably 2–300, and more preferably 2–100, and still more preferably 2 to about 10 molecules of detectable moieties per substrate.

In one embodiment, the electrophoretic tag moieties are attached to a "hub", to which the substrate (S) is also attached, as long as the presence of the hub does not interfere with enzymatic cleavage by the cell surface protease. The hub nucleus can be a polyfunctional material, normally polymeric, having a plurality of functional groups, e.g., hydroxy, amino, mercapto, carboxy, ethylenic, aldehyde, etc., as sites for linking. Illustrative hub nuclei include polysaccharides, polypeptides, such as polylysine, polynucleotides, ion exchange resins, and the like. The hub may also comprise a streptavidin, or like polyvalent molecule, that is bound to a biotin which is covalently linked to a substrate.

In one embodiment, a polysaccharide such as dextran, sepharose, polyribose, or polyxylose may be used. One specific example of a hub is dextran, to which about 10 to about 300 molecules of eTag moieties may be attached per one molecule of dextran. Another class of polymers includes polyalkylenes in which the monomers are substituted with hydrophilic groups; e.g. hydroxy, carboxy and the ester and amides thereof, amines, and the like. For example, the polyester formed from ethylene glycol and acrylic acid provides a hydroxyl group for derivatization to the components of the eTag probe. Other suitable polymers include polyallyl amines and alcohols such as, for example, polyvinyl alcohol. Copolymers may also be employed, e.g. a copolymer of polyethylene glycol with polyvinyl alcohol, in which hydrophilicity is provided by polyethylene glycol, and polyvinyl alcohol bears functional groups for reaction with the components of the eTag probe.

B. Preparation of Probes

The probe compositions can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the electrophoretic probes may include one or more steps of protection and deprotection (e.g., the formation and removal of acetal groups). In addition, the synthetic procedures can include various purifications, such as column chromatography, flash chromatography, thin-layer chromatography (TLC), recrystallization, distillation, high-pressure liquid chromatography (HPLC) and the like. Also, various techniques well-known in the chemical arts for the identification and quantification of chemical reaction products, such as proton and carbon-13 nuclear magnetic resonance (H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

In one embodiment, the charge-imparting moiety or mobility modifier is a peptide chain, linked to the peptide substrate, and such a conjugate (e.g. S-L-M-, where L is a bond or peptide fragment, and the conjugate is then linked to a detectable group) can be formed by well known methods of peptide synthesis. See, for example, Marglin et al., *Ann. Rev. Biochem.* 39:841–866 (1970). In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, *J. Am. Chem. Soc.* (1980) 85:2149–2154 and Houghten et a., *Int. J Pep. Prot. Res.* (1980) 16:311–320). A summary of the many techniques available for the synthesis of peptides may be found in J. M. Stewart et al., "Solid Phase Peptide Synthesis", W. H. Freeman Co, San Francisco (1969); and J. Meienhofer, "Hormonal Proteins and Peptides", (1973), vol. 2, p. 46, Academic Press (New York), for solid phase peptide synthesis; and E. Schroder et al., "The Peptides", vol. 1, Academic Press (New York), 1965 for solution synthesis.

Alternatively, the peptide can be linked to other classes of mobility modifiers as described above, e.g. oligomers of functionalized or charged monomers, or variously substituted aromatic groups, and further conjugated with a detectable group. The aforementioned labeled conjugates, having different electrophoretic mobilities, can be used in multiplexed assays as electrophoretic probes having specific cleavage sites. It is, of course, within the purview of the invention to prepare any number of labeled conjugates for performing multiplexed determinations.

IV. Kits

Another aspect of the present invention provides a kit comprising substrates of different ADAMs, each of which substrates is labeled with a different detectable label. Preferably, the substrates are provided as electrophoretic probes, wherein the labels are eTags, as described above.

The kit is useful in any of the multiplex assays described above. For example, the kit can be used to determine the effect of a given candidate effector on a variety of ADAMs at the same time, or to identify which ADAMs mediate the action of a given effector. Preferably, the detected product is an eTag reporter molecule. In particular, the kit contains electrophoretic probes comprising substrates for ADAM 10 and/or ADAM 17. A known substrate for ADAM 17 is TNF-α; accordingly, a fragment of TNF-α containing the cleavage site, such as the peptide having the sequence SPLAQAVRSSSR (SEQ ID NO: 2), can be used. A known substrate for ADAM 17 is CD40L; accordingly, a fragment of human CD40 surface protein having the cleavage site, such as the peptide KENSFEMQKGDQ (SEQ ID NO: 3), can be used.

The present invention also provides other kits in accordance with the various applications of the ADAM assay. For example, a kit comprising the substrate of an ADAM, as well as a plurality of candidate ligands, can be used to identify agonists and antagonists of an effector that is known to modulate the activity of the particular ADAM. A kit comprising the substrate of an ADAM that is known to cleave the APP at the α-secretase site, as well as a plurality of candidate modulating compounds, can be used to screen for drugs for treatment or prevention of Alzheimer's disease.

V. General Procedures for Assays Employing Electrophoretic Probes

The following general discussion of methods and examples of specific assays is by way of illustration and not limitation. One skilled in the art will be able to apply the technology herein in assaying for a variety of analytes in many assay formats known to the skilled artisan.

Conventional buffers may be used, such as phosphate, carbonate, HEPES, MOPS, Tris, borate, etc., as well as other conventional additives, such as salts, stabilizers, organic solvents, etc. The aqueous medium may be solely water or may include from 0.01 to 80 or more volume percent of a co-solvent.

The combined assay components are incubated for a time and at a temperature that permit a substantial number of binding events to occur. Generally, the time for incubation after combination of all or a portion of the reagents is at least 5 min, more usually at least 15 min, before adding further reagents.

Once a solution of cleaved eTag reporters is prepared and is free of any interfering components, the composition of the solution is analyzed. The released tags from an assay are preferably separated on a single separation medium or format, meaning that a sample mixture containing the combined tags is applied to a single separation medium, such as electrophoretic separation medium, a chromatography medium, or a mass spectroscopy medium, and all of the sample product/substrates components. are separated on that medium.

Preferably, electrophoretic tags in a plurality of tags are detected by electrophoretic separation and fluorescence. Preferably, electrophoretic tags having substantially identical fluorescence properties have different electrophoretic mobilities so that distinct peaks in an electropherogram are formed under separation conditions.

A measure of the distinctness, or lack of overlap, of adjacent peaks is electrophoretic resolution, which can be defined, in one of many ways, as the distance between adjacent peak maximums divided by four times the larger of the two standard deviations of the peaks. Preferably, adjacent peaks have a resolution, according to this definition, of at least 1.0, more preferably at least 1.5, and most preferably at least 2.0. In a given separation and detection system, the desired resolution may be obtained by selecting a plurality of electrophoretic tags whose members have electrophoretic mobilities that differ by at least a peak-resolving amount, such quantity depending on several factors well known to those of ordinary skill, including the signal detection system, the nature of the fluorescent moieties, the diffusion coefficients of the tags, the presence or absence of sieving matrices, nature of the electrophoretic apparatus, e.g. presence or absence of channels, length of separation channels, and the like.

Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Preferably, in such a conventional apparatus, the electrophoretic mobilities of a plurality of electrophoretic tags differ by at least one percent, and more preferably, by at least a percentage in the range of from 1 to 10 percent. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Conveniently, an aliquot, generally not more than about 5 µl, of assay solution is transferred to the sample reservoir of a microfluidics device or capillary electrophoretic device, either directly through electrophoretic or pneumatic injection into an integrated system or by syringe, capillary or the like. Microfluidics devices are described in a number of domestic and foreign Letters Patent and published patent applications. See, for example, U.S. Pat. Nos. 5,750,015; 5,900,130; 6,007,690; and WO 98/45693; WO 99/19717 and WO 99/15876. The conditions under which the separation is performed are conventional and will vary with the nature of the products. Longer times will be required for products that have similar mobilities under the conditions of the electrophoresis.

By way of illustration, FIG. 13 shows a microchannel network 100 in a microfluidics device of the type detailed in the application noted above, for sample loading and electrophoretic separation of a sample of probes and tags produced in the assay above. Briefly, the network includes a main separation channel 102 terminating at upstream and downstream reservoirs 104, 106, respectively. The main channel is intersected at offset axial positions by a side channel 108 that terminates at a reservoir 110, and a side channel 112 that terminates at a reservoir 114. The offset between the two side channel forms a sample loading zone 116 within the main channel.

Figure 13A:
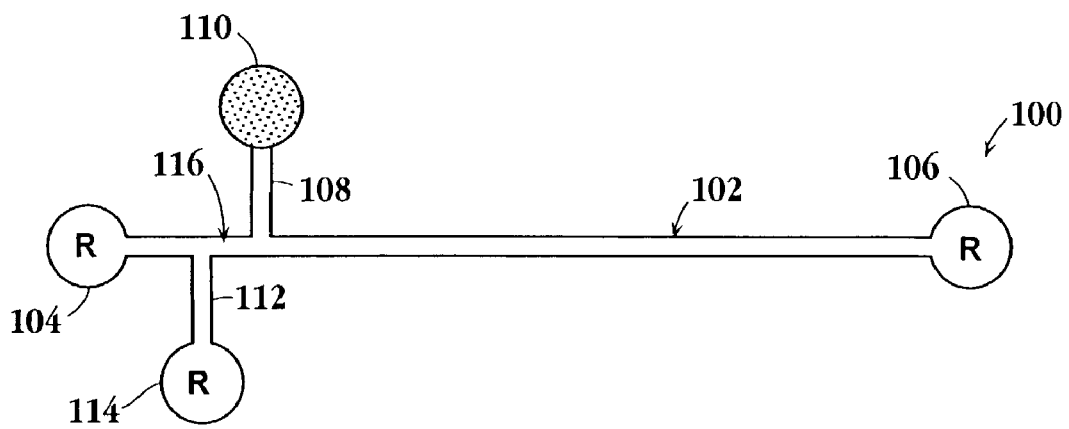
FIG. 13 shows steps in practicing the methods of the invention using a microfluidics/CE device.
Figure 13B:
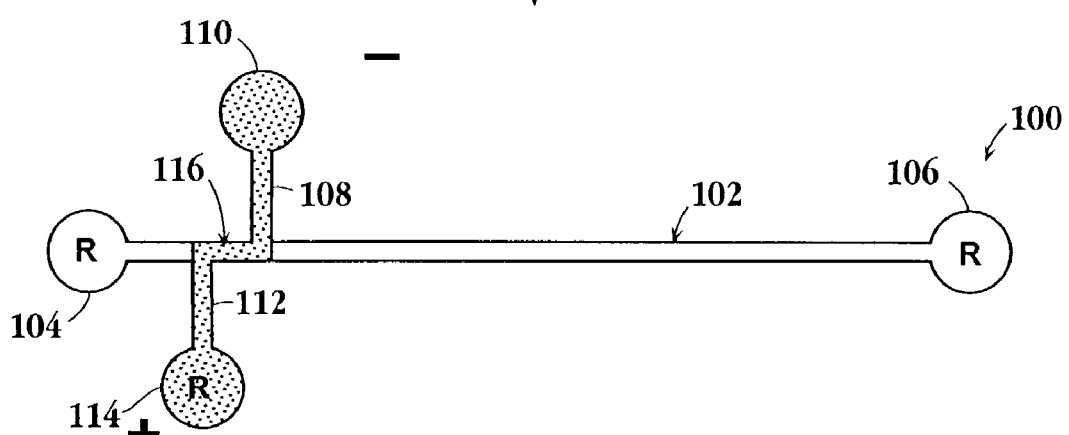
Figure 13C:
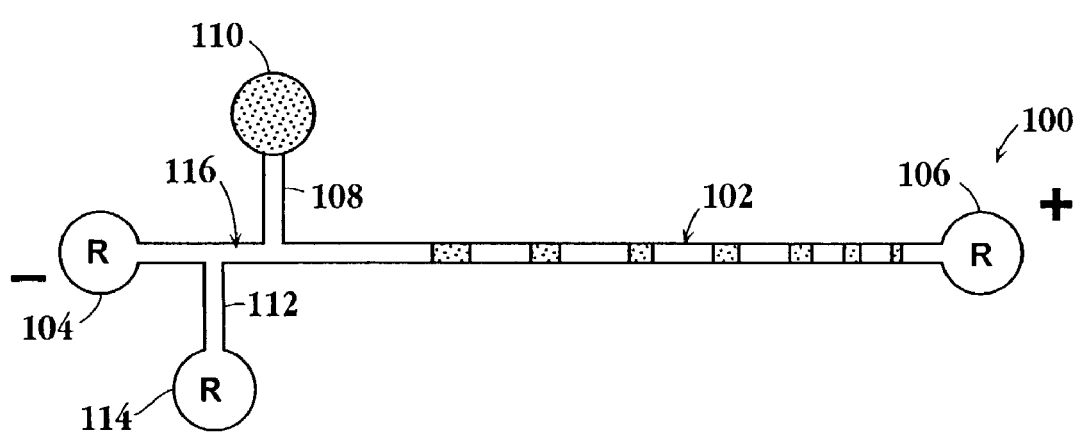

In operation, the assay mixture from above is placed in-sample reservoir 110, illustrated in FIG. 13A. As noted, the assay mixture contains one or more target cells with surface-bound electrophoretic probe, one or more test ligands, and optionally, an eTag standard. The assay reaction, involving initial ligand binding to target cell(s), followed by cleavage of probe linkers, may be carried out in sample reservoir 110, or alternatively, the assay reactions can be carried out in another reaction vessel, with the reacted sample components the added to the sample reservoir.

To load released eTags into the sample-loading zone, an electric field is applied across reservoirs 110, 114, as indicated in the Figure, drawing negatively charged released probes from reservoir 110 into loading zone 116 (FIG. 13B), while uncharged or positively charged sample components remain in the sample reservoir. The released tags in the loading zone can now be separated by conventional capillary electrophoresis (FIG. 13C), by applying an electric filed across reservoirs 104, 106, as indicated in the Figure.

From the resulting electrophoretic pattern, the tags, and corresponding cell types labeled by the tags, can be identified. This is typically done by placing a fluorescence detector near the downstream end of the separation channel, and constructing a electropherogram of the separated eTag components, first to determine the separation characteristic (in this case, electrophoretic mobility) as above, and secondly, to measure signal intensity, e.g., peak height or peak area, as a measure of the relative amount of tag associated with each probe. Methods for detecting and quantifying levels of a detectable probe are well known. In one preferred method, the tags are fluorescent labeled. A standard fluorescence-emission source is directed against a detection zone in a downstream portion of the separation medium, and fluorescence emission of the zone is measured by a standard light detector. The signal height or area recorded provides a measure of product and substrate concentration in the sample.

Addition of a known quantity of a control fluorophore to each sample before separation of the eTag reporters by electrophoresis allows conversion of relative fluorescent signals into absolute quantities. Any fluorophore that does not interfere with detection of the eTag reporter signals can be used for normalizing the fluorescent signal. The control signal will preferably have an electrophoretic mobility that is different from that of any of the eTag reporters in the sample, and may have the same or a different emission wavelength. Exemplary control fluorescent molecules include ROX, FAM, and fluorescein.

The following examples are offered to illustrate this invention and are not to be construed in any way as limiting the scope of the present invention.

EXAMPLES

The following abbreviations have the following meanings. Abbreviations not defined have their generally accepted meanings.

| | |
|---|---|
| ADAM = | a disintegrin and an metalloprotease |
| DMEM = | Dulbecco's modified Eagle's medium |
| EGF = | epidermal growth factor |
| FBS = | fetal bovine serum |
| FRET = | fluorescence resonance energy transfer |
| GPCR = | G-protein coupled receptor |
| LPA = | lysophosphatidic acid |
| MEM = | modified Eagle's medium |
| MT-MMP = | membrane-type matrix metalloprotease |
| PBS = | phosphate buffered saline |
| PDGF = | platelet derived growth factor |
| PEO = | polyethyene oxide |
| PMA = | phorbol myristate acetate |
| PMT = | photormultiplier tube |
| RFU = | relative fluorescence unit |
| TACE = | tumor necrosis factor α converting enzyme |
| TNF-α = | tumor necrosis factor α |
| HANKS = | Hanks balanced salt solution |

Exemplary Assay Protocol

A substrate for a cell surface protease, typically an ADAM, or preferably a plurality of substrates for different proteases, each having a distinct detectable label, is added to a live cell suspension in a buffer. Typically, about $1.5 \times 10^5$ cells are used in 50 μL medium. However, the methods of the present invention allow the use of as few as 40 cells, in 2 μL medium. The cells are washed three times on ice with buffer (lacking the protein and anti-proteases noted below) before use. A suitable buffer consists of 50 mM HEPES (pH 7.2), 150 mM NaCl, 2 mM $MgCl_2$, 0.1% human serum albumin (HSA), with serine and thiol protease inhibitor cocktail (Roche Diagnostics). Depending on the peptide, nonspecific binding may be blocked by addition of a protein selected from human serum albumin (HSA), bovine serum albumin (BSA), casein (CAS), gamma globulins (GG), and fetal bovine serum (FBS).

All component additions are done on ice, and the tubes are then transferred to a temperature controlled water bath for incubation. The assay mixture is incubated at a fixed temperature for a fixed time, e.g., 37° C. for 1 hr. Following incubation, the tubes are removed from the incubator and placed again on ice. One or more electrophesis standards, e.g. aminomethyl fluorescein, is added, and the mixture is analyzed by electrophoresis, preferably on a microfluidic card or "chip".

For experiments employing additional reagents, such as a GPCR agonist or a protein kinase C stimulator such as PMA (phorbol myristate acetate), the additional reagent is added at the beginning of the incubation period.

For experiments involving GPCR's, adherent cells are plated into 96-well plates at $5 \times 10^4$ cells/well and serum starved for 18–24 hr prior to use. A suitable buffer comprises 10 mM HEPES (pH 7.2), 1× HANKS, 0.1% human serum albumin (HSA), and serine/thiol protease inhibitor cocktail (Roche Diagnostics). Cells are washed three times with the HANKS-HEPES buffer, lacking protein and anti-protease, prior to use.

Protocol for Analysis of Assay Products

The products of the assays are conveniently analyzed by capillary electrophoresis on a microfluidic LabCard™ (ACLARA Biosciences, Inc.). Typically, a LabCard™ containing a 64-channel array is used, but no special changes are needed to run the assay on a 96- or 32-channel card, or other configuration.

The configuration of channels for each separation on a LabCard is shown schematically in FIG. 13. The channel network may be a double-T network as shown or a cross network, i.e. where wells 110 and 114 in the figure are directly opposed. A suitable separation medium consists of 1% PEO in 50 mM HEPES (pH 7.2). In a typical separation, sample is injected from well 110 to well 114 at an injection voltage of 550V for e.g. 35 sec. Separation is carried out from well 104 to well 106 for e.g. 20 sec., with the voltages of 0V, 380V, 800V, and 380V in wells 104, 110, 106, and 114, respectively, resulting in a field strength of 455V/cm. In a typical separation, detection occurs at 5 mm down from the injection site (cross), an argon-ion laser is used as the excitation source, PMT is typically set at 600V to 900V, and gain is set to 5 µA/V at a frequency of 10 Hz. The 10× objective is used, and the sampling rate is 200/sec. Well volumes are typically 2 µL.

For peak analysis, time normalized peak areas for peptide cleavage products are divided by time normalized fluorescein (or aminomethyl fluorescein) peak areas to arrive at the product/fluorescein normalized area ratios.

Example 1

Detection of Cleavage of TNF-α by ADAM 17

A TNF-α peptide fragment, known to be a substrate for ADAM 17, was labeled at the N-terminus with fluorescein. This compound, 5-carboxyfluorescein-SPLAQAVRSSSR-amide, was designated TNF-α-FL, and the amino acid sequence is designated SEQ ID NO: 2. The compounds was added to THP-1 cells, which are known to possess relatively large quantities of ADAM 17. After a one-hour incubation, aminomethyl fluorescein was added as an electrophoretic marker, and the reaction supernatant was separated by capillary electrophoresis.

FIG. 2 shows a typical cleavage pattern obtained with these cells. The peak marked "product" has a mobility consistent with the theoretical mobility of the putative cleavage fragment, as calculated from its mass and charge. The product was not present in the absence of cells, indicating that a cellular component caused the substrate to be cleaved.

Figure 3:
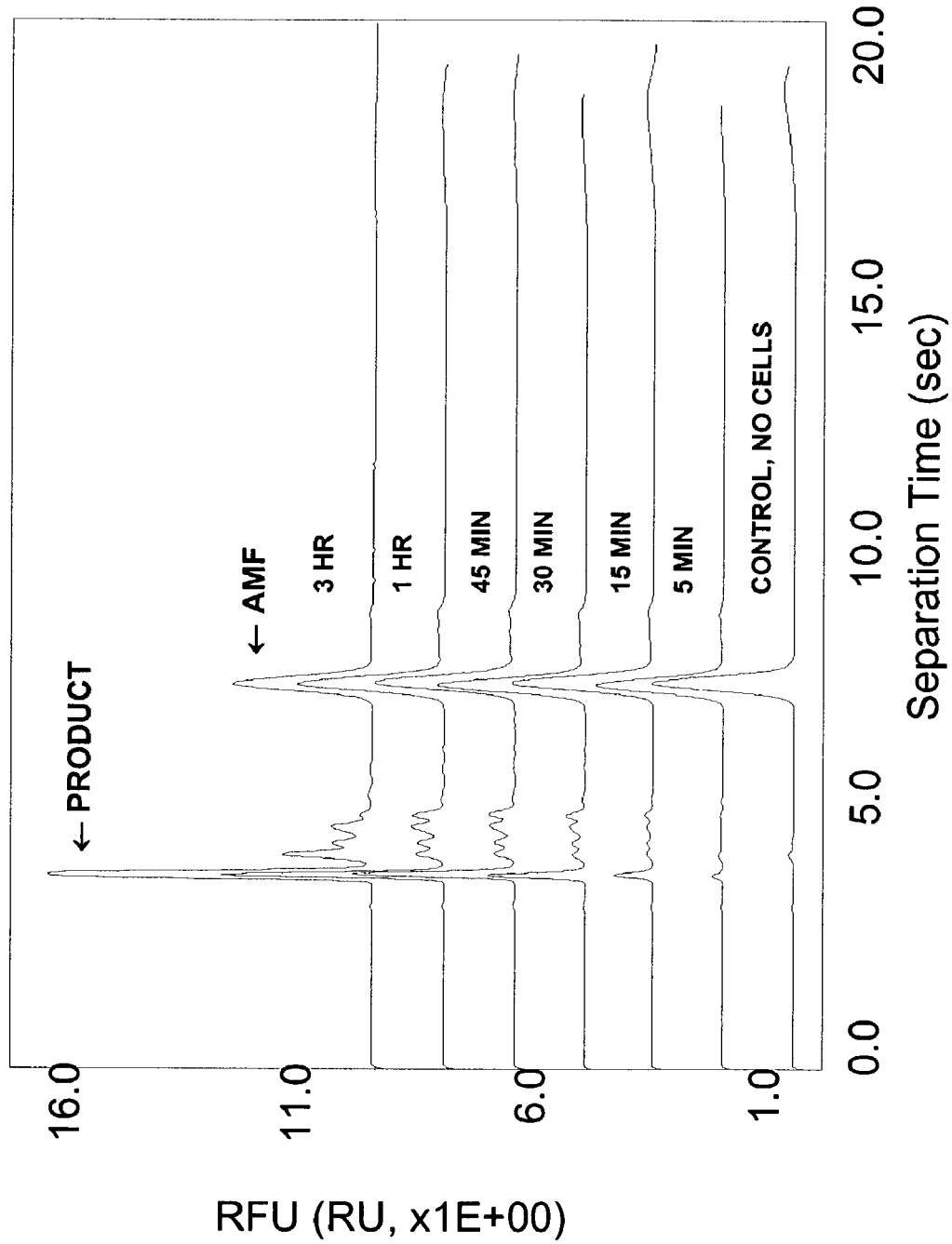
FIG. 3 shows the results of a time course experiment wherein an ADAM assay was performed over various lengths of time, in accordance with one embodiment of the invention.
Figure 4:
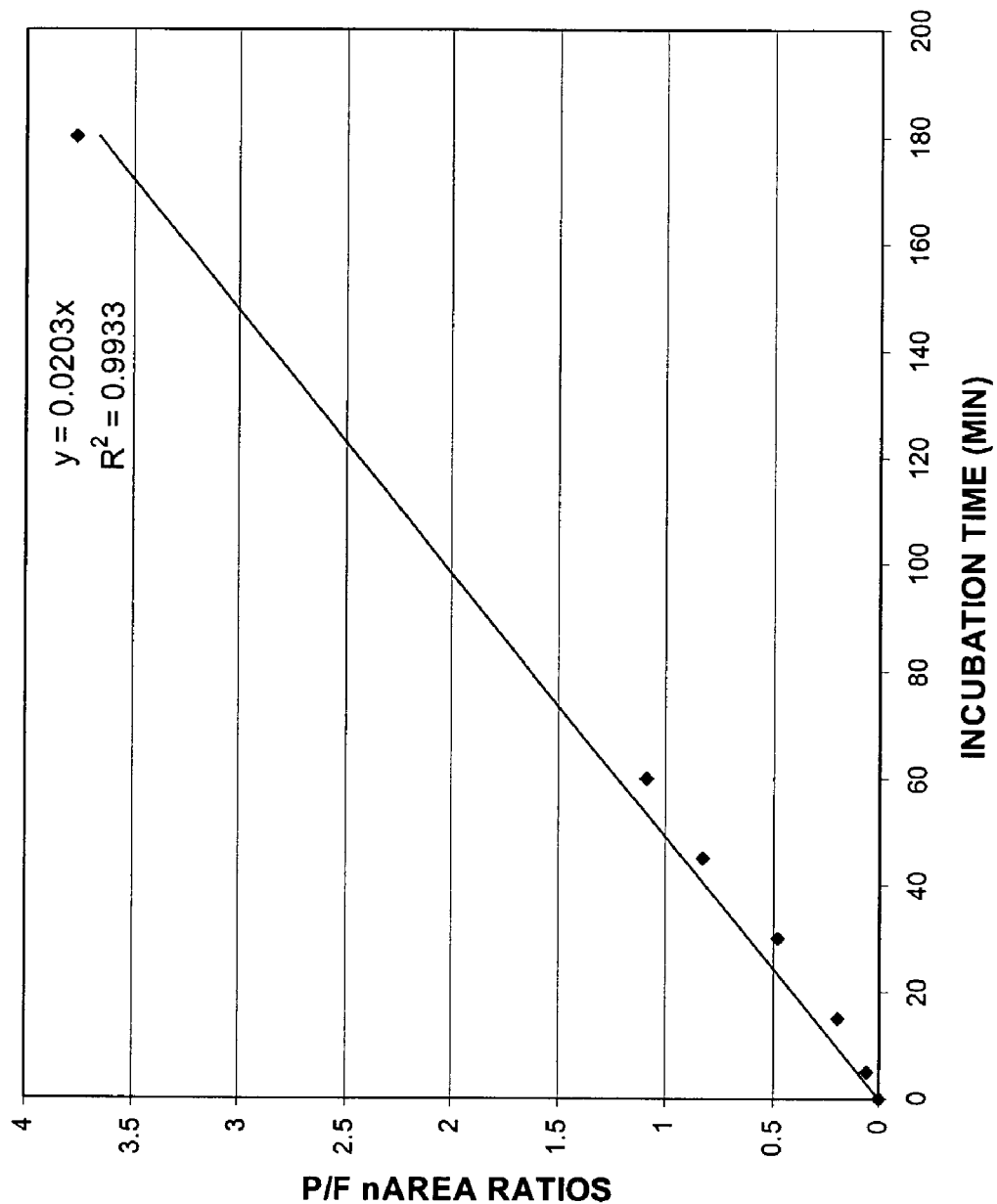
FIG. 4 shows the plot of the data obtained in the time course experiment shown in FIG. 3.
Figure 5:
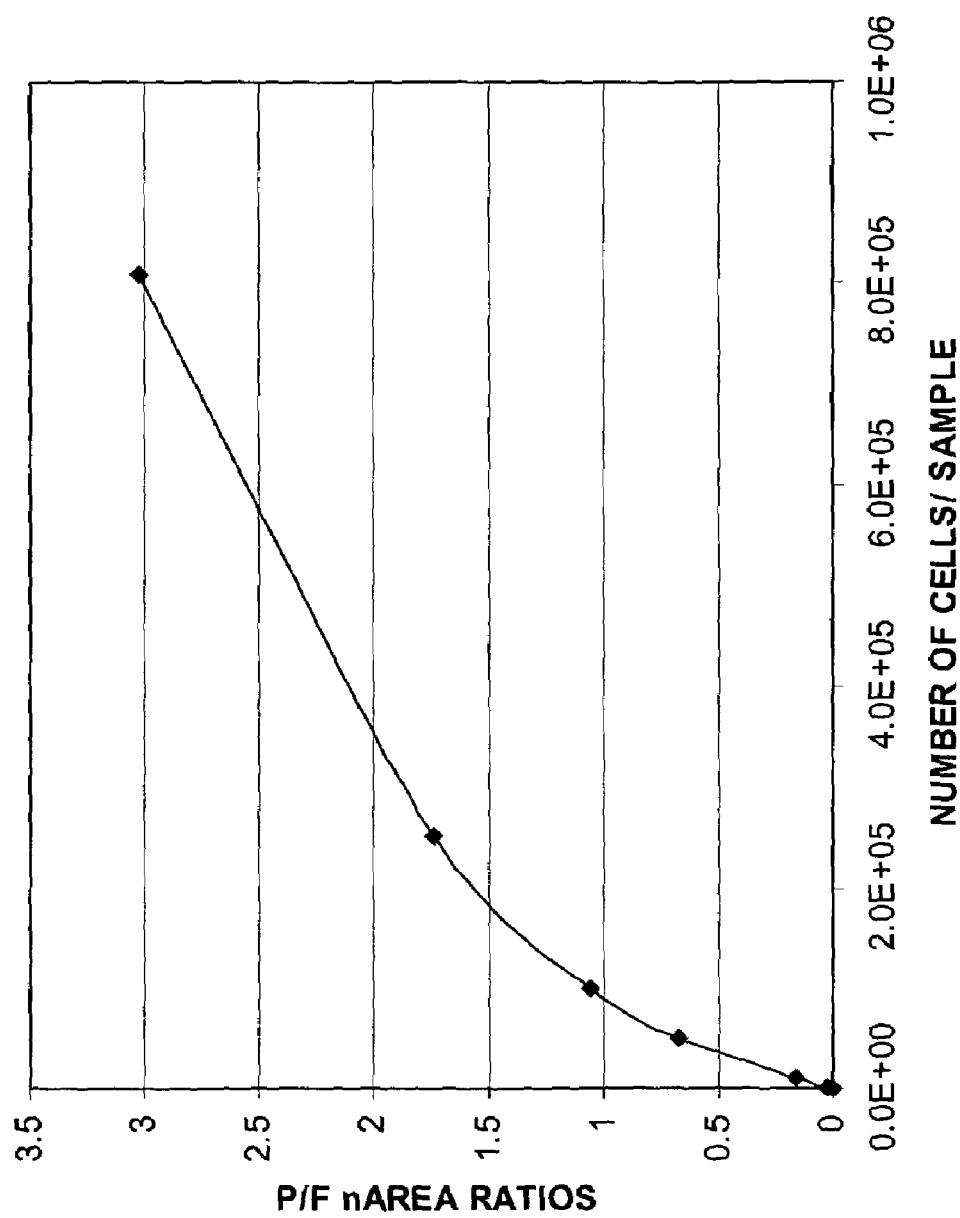
FIG. 5 shows a dose response of the ADAM assay, wherein increasing numbers of cells were incubated with the substrate.

FIG. 3 shows the cleavage response as a function of increasing incubation time. As the incubation time increased from 5 min to 3 hr, there was a linear increase in product formation (FIG. 4). A dose-response experiment, based on increasing cell number, was also performed. The data are shown in FIG. 6, which demonstrates that the amount of product increased with the number of cells, and that the dose response was linear when the number of cells were $5 \times 10^4$ or less, under the conditions of this assay.

GM6001, a metalloprotease inhibitor, was used to confirm that the substrate was indeed cleaved by a metalloprotease. As shown in FIG. 6, GM6001 completely inhibited formation of the cleavage product, indicating that cleavage was due to the presumed metalloprotease activity.

The protein kinase C activator phorbol myristate acetate (PMA) is reported to cause internalization of cell surface ADAM 17 in THP-1 cells (Doedens and Black, 2000). Therefore, PMA should reduce the amount of cleavage product if it is added to the assay system described above. Indeed, in the presence of PMA (FIG. 7), the level of TNF-α-FL cleavage product was significantly lower than that in the absence of PMA, further indicating that the cell surface metalloprotease ADAM 17 was responsible for the detected cleavage product.

The same study reported that sucrose, at 450 mM, inhibits clathrin-coated pit mediated uptake of cell surface molecules and receptors, and that PMA-induced internalization of ADAM 17 is inhibited by 450 mM sucrose. As shown in FIG. 8, PMA significantly reduced TNF-α-FL cleavage, but the addition of sucrose restored the activity, confirming that the assay is specific for cell surface ADAM 17 activity.

Taken together, these results demonstrate that the methods of the invention provide a specific cell surface ADAM assay with a linear time course of cleavage and a dose response based on cell number.

Example 2

Determination of Ligand Effects on GPCR Activity, via Measurement of ADAM 10 Activity The methods of the invention can also be used to determine the activity of an effector that is functionally associated with an ADAM. For example, ADAM 10 has been reported to mediate the transactivation of EGF receptor by a GPCR (Yan et al., 2000). The activity of the GPCR can thus be determined by measuring ADAM 10 activity. Furthermore, putative agonists or antagonists of the GPCR can also be added to this assay system to determine their effects on the GPCR, which would be reflected by a change in the cognate ADAM activity.

Three known ligands for GPCRs, endothelin-1, LPA and carbachol, were employed to demonstrate the effectiveness of the assay in reflecting the effect of each ligand on its cognate GPCR. PMA was also tested for its effect on ADAM 10 activity.

Rat-1 cells, which are known to have ADAM 10 at the cell surface, were combined with a substrate derived from CD40L (5-carboxyfluorescein-KENSFEMQKGAQ-amide; designated CD40L-FL, and having an amino acid sequence desginated SEQ ID NO: 3). Different ligands were added, each of which is known to modulate the GPCR, which in turn transactivates the EGF receptor via ADAM 10.

Figure 9:
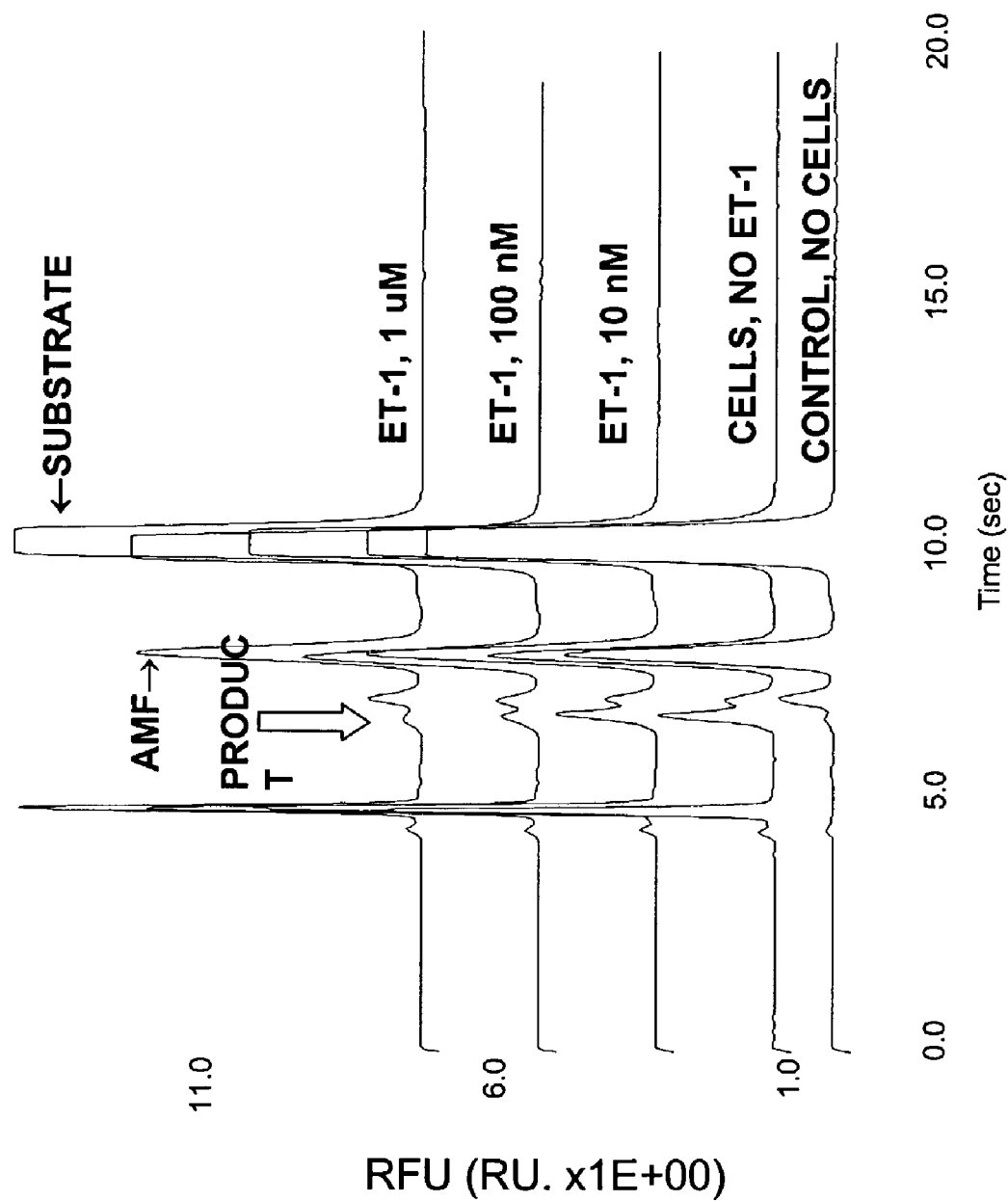
FIG. 9 shows the separation profile of cells treated with varying concentrations of endothelin-1.

FIG. 9 shows electropherograms generated from separation of reaction materials from cells treated with endothelin-1. Although the signal generated from reaction product is only a minor component of the overall signal, the product could be detected in very small quantities because it could be resolved from other background signals. It is thus apparent that, even with singleplex assays, separation of the products of the reaction before quantitation leads to a dramatic improvement in the sensitivity of the assay.

Figure 10:
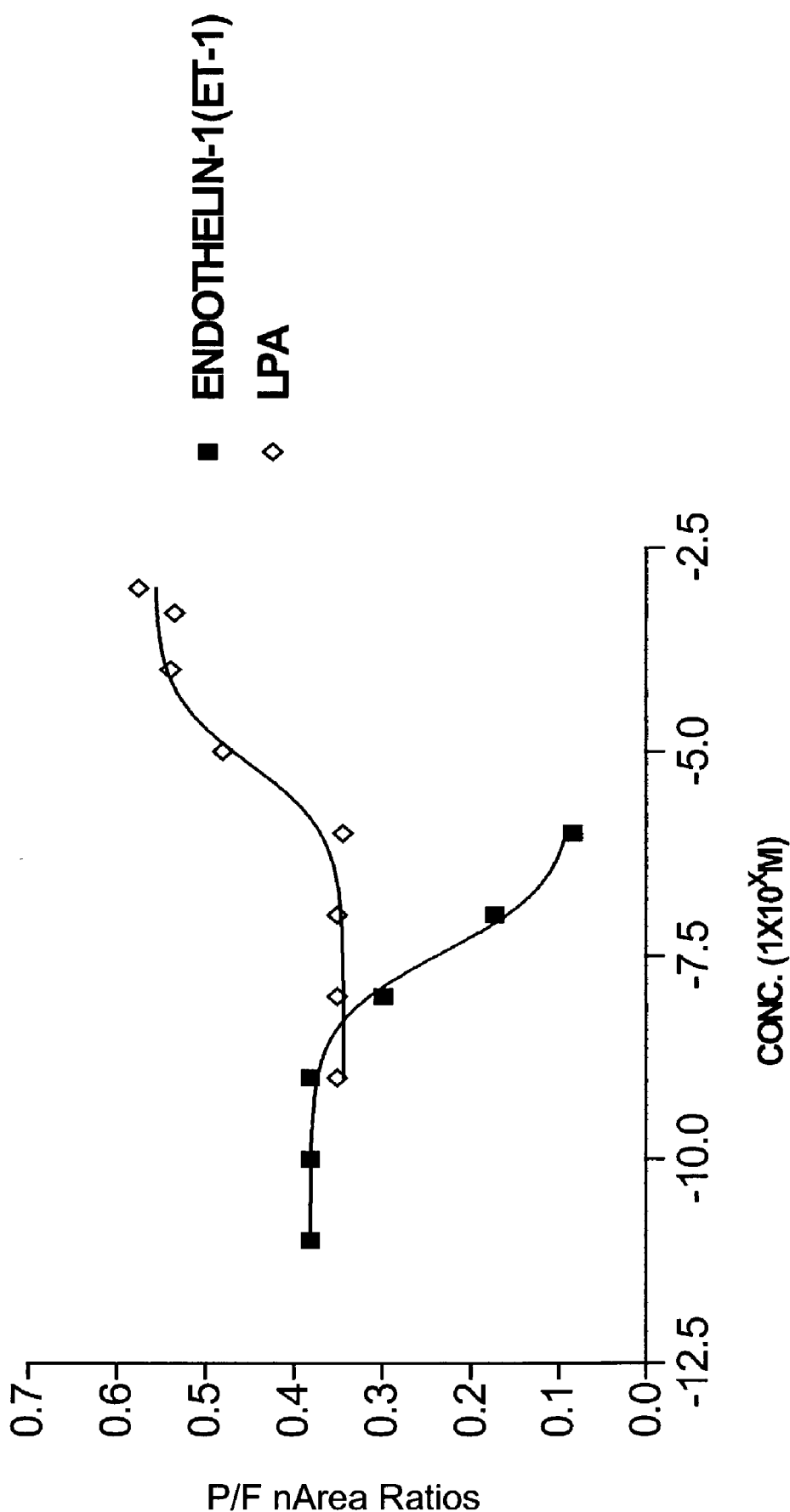
FIG. 10 shows the effect of endothelin-1 and LPA, each being capable of binding to a GPCR, on the activity of ADAM 10.
Figure 11:
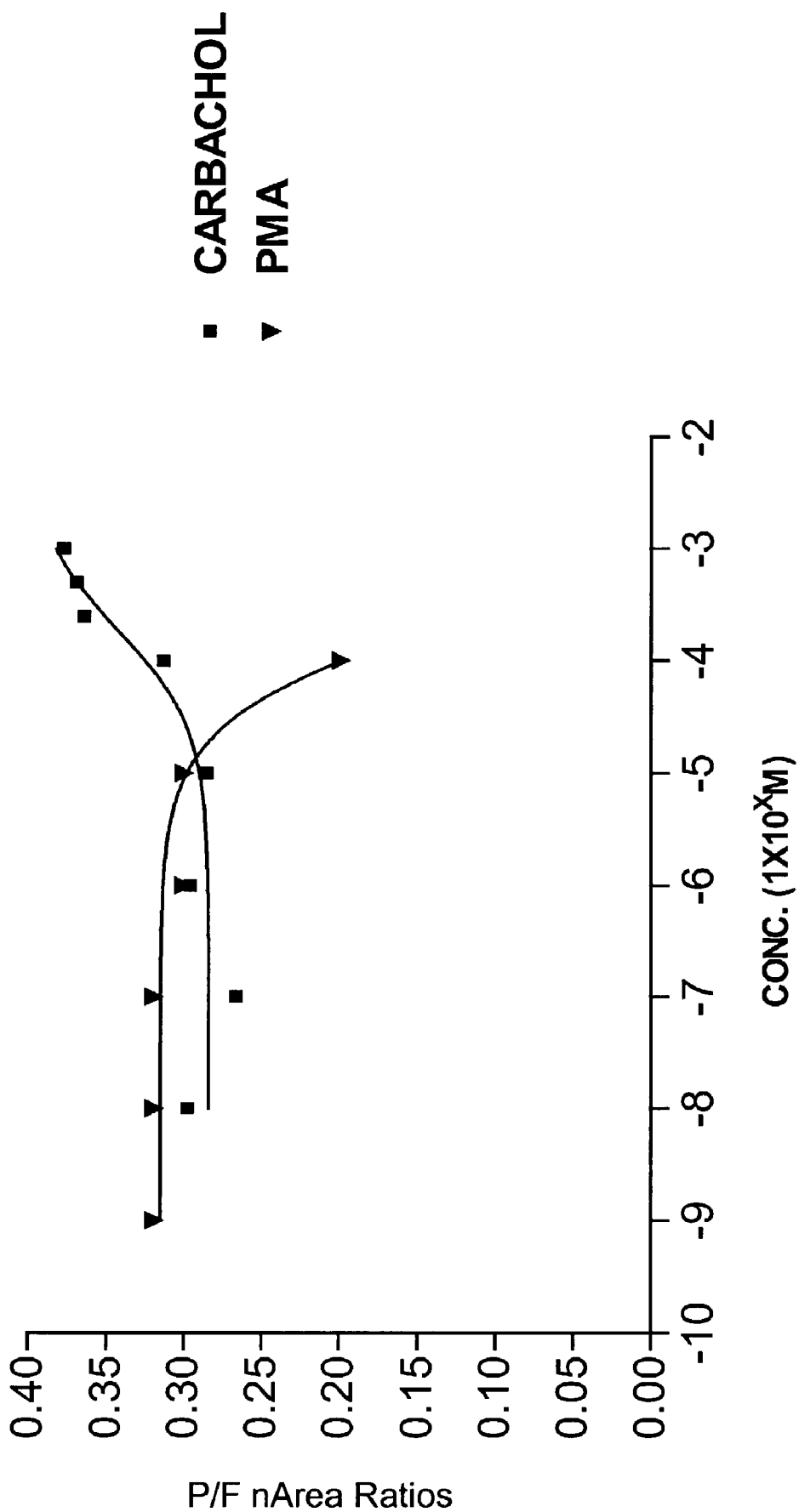
FIG. 11 shows the effects of carbachol (a GPCR ligand) and PMA on the activity of ADAM 10.

The amount of product for both LPA and endothelin-1 treated cells was quantitated. LPA increased ADAM 10 activity while endothelin-1 decreased it, as expected (FIG. 10).

Figure 12:
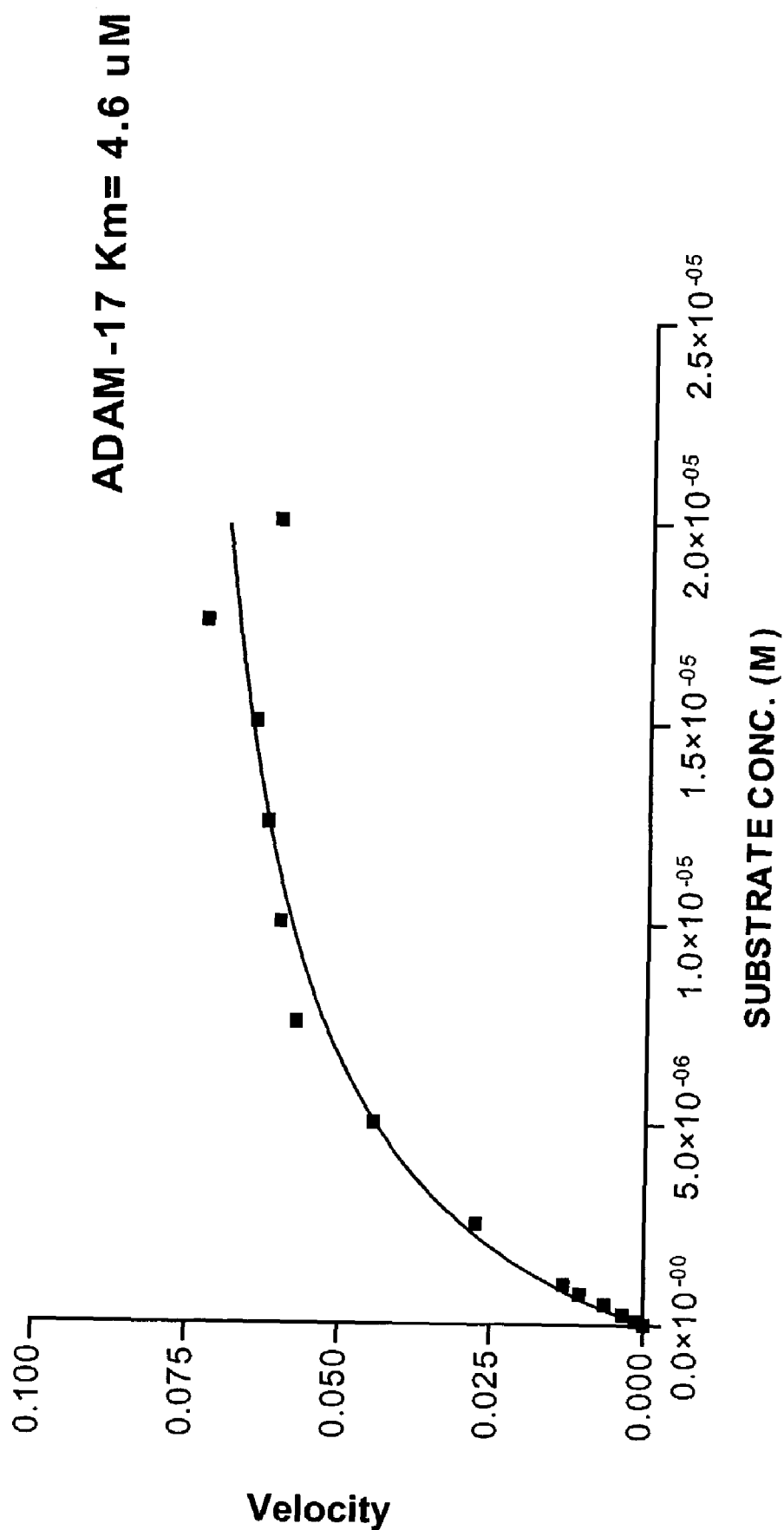
FIG. 12 shows the results of a kinetic study using the present whole cell assay.

The assay was also performed in HEK-293 cells, another cell line known to contain ADAM 10. As expected, carbachol activated ADAM 10 activity, and PMA resulted in a decline, presumably by causing the cell surface ADAM 10 to internalize (FIG. 12).

The present method can therefore be used to assay for an effector that positively or negatively affects the activity of an ADAM, whether the modulation is achieved directly or indirectly. The present method is also demonstrated to be useful in assaying for agonists or antagonists of a given effector, using a known ADAM and its cognate substrate. Moreover, the present assay can be performed using various cell types for a number of ligands and/or GPCRs. Of particular significance, the disclosed method is highly sensitive, and consequently allows measurement of GPCRs at their normal endogenous levels, rather than requiring transfection, as is used in the previous state of the art to increase GPCR expression and thus the signal produced by the assay.

Example 3

Kinetic Study Using the ADAM Assay

The present invention can also be used in kinetic studies of ADAM activity. To this end, THP-1 cells expressing high levels of the ADAM 17 protein were incubated with varying concentrations of substrate, and the velocity of the protease cleavage reaction was determined. The velocity was plotted against the concentration in each reaction (FIG. 12), and the Km was calculated to be 4.6 μM (similarly, other kinetic parameters can be measured).

It is worth noting that kinetic studies are conventionally performed, in the present state of the art, with purified enzymes or substantially purified enzymes in order to obtain clear results. If cell lysates, which contain many other cellular factors, are used, the data are typically too variable to allow calculation of an accurate $K_m$. Whole cell systems also do not usually result in clear kinetic data.

In contrast, the present assay is a whole cell assay; therefore, the reaction can be performed and products detected without interference from factors from inside the cell. Therefore, the present invention provides a significantly improved method for kinetic studies.

3. The method of claim 2, wherein the substrate is cleavable by the ADAM to release a product comprising the detectable label.

4. The method of claim 1, wherein said step of separating the substrate and the product is performed by chromatographic means or by electrophoresis.

5. The method of claim 4, wherein the step of separating is performed using capillary electrophoresis or electrophoresis on a microfluidic device.

6. The method of claim 1, wherein the cells have endogenous levels of the ADAM.

7. The method of claim 1, wherein the whole cell system comprises less than about $10^4$ cells per assay.

8. The method of claim 1, wherein the whole cell system comprises less than about $10^3$ cells per assay.

We claim:

1. A method of assaying for the activity of an ADAM (a disintegrin and metalloprotease) in a whole cell system, comprising:
   (a) selecting a soluble substrate that ADAM specifically cleaves;
   (b) combining the soluble substrate with the whole cell system under conditions that allow processing of the substrate to a product by the ADAM;
   (c) separating the substrate and the product; and
   (d) determining the amount of the product as an indication of the ADAM activity.

2. The method of claim 1, wherein the substrate contains a detectable label.

9. The method of claim 1, wherein the whole cell system comprises less than about 500 cells per assay.

10. The method of claim 1, wherein the whole cell system comprises less than about 50 cells per assay.

11. The method of claim 2, wherein the ADAM is selected from the group consisting of ADAM 10 and ADAM 17.

12. A method of assaying the activities of a plurality of ADAMs in a whole cell system, comprising
   selecting a plurality of soluble substrates, said plurality comprising at least one substrate that each ADAM specifically cleaves to a product to be assayed,
   combining said substrates with said whole cell system, under conditions that allow processing of the substrates to products by the corresponding ADAMs, such that each ADAM produces a different product;

and determining the amount of each product, as an indication of the corresponding ADAM activity.

13. The method of claim 12, wherein each substrate is an electrophoretic probe comprising an electrophoretic tag, said tag having distinct optical or separation properties with respect to the electrophoretic tag of every other probe used in the assay; and each said probe is cleavable by the corresponding ADAM to release the electrophoretic tag.

14. The method of claim 13, wherein each said electrophoretic probe is of the form S-L-(D-M), where:
   S is a substrate peptide cleavable by the corresponding ADAM;
   (D-M) represents an electrophoretic tag, where
      D is a detectable group and
      M is a mobility modifier effective to impart to the electrophoretic tag a known electrophoretic mobility different from the mobility of the electrophoretic tag of any other probe employed in the assay; and
   L is a bond or linking group connecting the substrate peptide to the electrophoretic tag.

15. A method for determining the effect of a candidate effector on the activity of an ADAM in a whole cell system, comprising:
   (a) selecting a soluble substrate that ADAM specifically cleaves;
   (b) preparing two mixtures of the whole cell system and the soluble substrate, wherein only one of the mixtures contains the candidate effector;
   (c) incubating the mixtures under conditions that allow processing of the substrate to a product by the ADAM, if the ADAM is active;
   (d) determining the amount of the product formed in each mixture; and
   (e) comparing the amount of product formed in the separate mixtures to determine the effect of the candidate effector on the ADAM activity.

16. The method of claim 15, wherein the candidate effector is a receptor.

17. The method of claim 16, wherein the receptor is a G-protein coupled receptor (GPCR).

18. The method of claim 15, wherein the substrate contains a detectable label.

19. The method of claim 18, wherein the substrate is cleavable to release a product comprising the detectable label.

20. The method of claim 19, further comprising the step of separating the substrate and the product before determining the amount of the product.

21. The method of claim 20, wherein the step of separating is performed using capillary electrophoresis.

22. The method of claim 15, wherein the cells have endogenous levels of said ADAM.

23. The method of claim 15, for use in determining the effect of a candidate effector on the activity of a plurality of ADAMs from a whole cell system,
   wherein a plurality of said soluble substrates, comprising at least one substrate that is specifically cleavable to a product by each ADAM to be assayed, is combined with said whole cell system in two mixtures, where one of the mixtures contains the candidate effector; and the amount of each product formed in the two mixtures is compared, to determine the effect of the candidate effector on the activity of each ADAM.

24. The method of claim 23, wherein each substrate is an electrophoretic probe comprising an electrophoretic tag, said tag having distinct optical or separation properties with respect to the electrophoretic tag of every other probe used in the assay; and each said probe is cleavable by the corresponding ADAM to release the electrophoretic tag.

25. The method of claim 24, wherein each said electrophoretic probe is of the form S-L-(D-M), where:
   S is a substrate peptide cleavable by the corresponding ADAM;
   (D-M) represents an electrophoretic tag, where
      D is a detectable group and
      M is a mobility modifier effective to impart to the electrophoretic tag a known electrophoretic mobility different from the mobility of the electrophoretic tag of any other probe employed in the assay; and
   L is a bond or linking group connecting the substrate peptide to the electrophoretic tag.

26. A method for determining the effect of a candidate ligand on a receptor in a whole cell system comprising an ADAM, wherein the receptor is known to activate or inhibit the activity of said ADAM, comprising:
   (a) selecting a soluble substrate that ADAM specifically cleaves;
   (b) preparing two mixtures of the whole cell system and the soluble substrate, wherein only one of the mixtures contains the candidate ligand;
   (c) incubating the mixtures under conditions that allow processing of the substrate to a product by the ADAM, if the ADAM is active;
   (d) determining the amount of the product formed in each mixture; and
   (e) comparing the amount of product formed in the separate mixtures, to determine the effect of the candidate ligand on the receptor.

27. The method of claim 26, wherein the receptor is a GPCR.

28. The method of claim 27, wherein the substrate contains a detectable label.

29. The method of claim 28, wherein the substrate is cleavable to release a product comprising the detectable label.

30. The method of claim 29, further comprising the step of separating the substrate and the product before determining the amount of the product.

31. The method of claim 30, wherein the step of separating is performed using capillary electrophoresis.

32. The method of claim 26, wherein the cell system has endogenous levels of the ADAM.

33. A method of determining the effect of a G-protein coupled receptor (GPCR) on the activity of an ADAM in a whole cell system, comprising:
   (a) selecting a ligand known to activate or inhibit activity of the GPCR and a soluble substrate that ADAM specifically cleaves;
   (b) preparing two mixtures of the whole cell system and the soluble substrate, wherein only one of the mixtures contains the ligand;
   (c) incubating the mixtures under conditions that allow processing of the substrate to a product by the ADAM, if the ADAM is active;
   (d) determining the amount of the product formed in each mixture; and
   (e) comparing the amount of product formed in the separate mixtures to determine the effect of the GPCR on the ADAM activity.

34. The method of claim 33, wherein the cells have endogenous levels of said ADAM.

35. The method of claim 33, for determining the effect of a G-protein coupled receptor (GPCR) on the activity of a plurality of ADAMs in a whole cell system, wherein a plurality of soluble substrates, comprising at least one substrate that each ADAM specifically cleaves to be assayed, is added to said whole cell system in two mixtures, of which only one contains said ligand;

and the amount of each product formed in the separate mixtures is compared, to determine the effect of the GPCR on the activity of each ADAM.

36. The method of claim 35, wherein each substrate is an electrophoretic probe comprising an electrophoretic tag, said tag having distinct optical or separation properties with respect to the electrophoretic tag of every other probe used in the assay; and each said probe is cleavable by the corresponding ADAM to release the electrophoretic tag.

37. The method of claim 36, wherein each said electrophoretic probe is of the form S-L-(D-M), where:
    S is a substrate peptide cleavable by the corresponding ADAM;
    (D-M) represents an electrophoretic tag, where
        D is a detectable group and
        M is a mobility modifier effective to impart to the electrophoretic tag a known electrophoretic mobility different from the mobility of the electrophoretic tag of any other probe employed in the assay; and
    L is a bond or linking group connecting the substrate peptide to the electrophoretic tag.

38. A method for determining the effect of a compound on cleavage of the β-amyloid precursor protein (APP) at the α-secretase site in a whole cell system, comprising:
    (a) selecting an enzyme that cleaves the β-amyloid precursor protein at the α-secretase site in the whole cell system;
    (b) selecting a soluble substrate having a cleavable α-secretase site;
    (c) preparing two mixtures of the soluble substrate and the whole cell system, wherein only one of the mixtures contains the compound;
    (d) incubating the mixtures under conditions that allow cleavage of the substrate at the α-secretase site;
    (e) determining the amount of cleavage of the substrate in each mixture; and
    (f) comparing the amount of cleavage in the separate mixtures, to determine the effect of the compound on cleavage of APP.

39. The method of claim 38, wherein the substrate contains a detectable label.

40. The method of claim 39, wherein the substrate is cleavable to release a product comprising the detectable label.

41. The method of claim 38, wherein the enzyme is ADAM 17 or ADAM 10.

42. The method of claim 38, wherein the substrate having a cleavable α-secretase site is a fragment of human β-amyloid precursor protein.

43. A kit comprising
    a soluble substrate for an ADAM and
    a candidate effector for ADAM activity.

44. The kit of claim 43, comprising
    a plurality of soluble substrates, each substrate being specific for a different ADAM, and
    a plurality of candidate effectors for ADAM activity.

45. The kit of claim 44, where each said substrate further comprises an electrophoretic tag, having a detectable group and a mobility modifier effective to impart to the electrophoretic tag a known electrophoretic mobility different from the mobility of the electrophoretic tag of any other substrate employed in the assay.

46. A method of assaying for the activity of a plurality of cell surface ADAM proteases in a whole cell system, comprising:
    (a) providing, for each protease being assayed, a soluble substrate the protease specifically cleaves,
    (b) combining the substrates with the whole cell system under conditions that allow processing of each substrate to a product by the respective protease; and
    (c) electrophoretically separating and determining the amount of each product, as an indication of the activity of the corresponding protease;
    wherein each substrate is an electrophoretic probe comprising an electrophoretic tag, said tag having distinct optical or separation properties with respect to the electrophoretic tag of every other probe used in the assay; and each said probe is cleavable by the corresponding protease to release the electrophoretic tag.

47. The method of claim 46, wherein the whole cell system has endogenous levels of said proteases.

* * * * *